(12) United States Patent
Nishikawa et al.

(10) Patent No.: US 9,575,060 B2
(45) Date of Patent: Feb. 21, 2017

(54) METHOD FOR DETECTING A TARGET PARTICLE

(71) Applicant: OLYMPUS CORPORATION, Tokyo (JP)

(72) Inventors: Kazutaka Nishikawa, Tokyo (JP); Takuya Hanashi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 183 days.

(21) Appl. No.: 14/465,208

(22) Filed: Aug. 21, 2014

(65) Prior Publication Data
US 2014/0356969 A1 Dec. 4, 2014

Related U.S. Application Data

(63) Continuation of application No. PCT/JP2013/052110, filed on Jan. 30, 2013.

(30) Foreign Application Priority Data

Apr. 18, 2012 (JP) .................................. 2012-095101

(51) Int. Cl.
*G01N 21/64* (2006.01)
*G01N 21/76* (2006.01)
(Continued)

(52) U.S. Cl.
CPC ...... *G01N 33/5308* (2013.01); *G01N 15/1434* (2013.01); *G01N 21/6486* (2013.01);
(Continued)

(58) Field of Classification Search
CPC ............. G01N 15/1434; G01N 21/64; G01N 21/6486; G01N 21/76; G01N 2201/12; G01N 33/52; G01N 33/5308; G01N 33/54313; G02B 21/00; G02B 21/0076; Y10T 436/143333
(Continued)

(56) References Cited

U.S. PATENT DOCUMENTS

| 4,251,733 A | 2/1981 | Hirleman, Jr. |
| 5,308,990 A | 5/1994 | Takahashi et al. |

(Continued)

FOREIGN PATENT DOCUMENTS

| CN | 101503734 A | 8/2009 |
| EP | 1 906 172 A1 | 4/2008 |

(Continued)

OTHER PUBLICATIONS

Extended European Search Report dated Oct. 26, 2015, issued in counterpart European Patent Application No. 13777928.6 (7 pages).
(Continued)

*Primary Examiner* — Maureen Wallenhorst
(74) *Attorney, Agent, or Firm* — Westerman, Hattori, Daniels & Adrian, LLP

(57) ABSTRACT

Provided is a method for detecting a target particle that is a method for detecting a non-luminescent target particle dispersed and randomly moving in a sample solution using an optical system of a confocal microscope or multi-photon microscope, having: (a) preparing a sample solution containing target particles, and labeling particles of which the average outer diameter is less than 15% of the diameter of a photodetection region of the optical system, binding two or more molecules of the labeling particles per molecule of the target particles in the sample solution, and forming a non-luminescent complex of which the outer diameter is 15% or more of the diameter of the photodetection region; and, (b) calculating the number of molecules of the complex in the sample solution prepared in the (a) using an inverse scanning molecule counting method.

12 Claims, 10 Drawing Sheets

(51) Int. Cl.
  *G01N 33/52* (2006.01)
  *G01N 33/53* (2006.01)
  *G02B 21/00* (2006.01)
  *G01N 33/543* (2006.01)
  *G01N 15/14* (2006.01)

(52) U.S. Cl.
  CPC ............ *G01N 21/76* (2013.01); *G01N 33/52* (2013.01); *G01N 33/54313* (2013.01); *G02B 21/00* (2013.01); *G02B 21/0076* (2013.01); *G01N 2201/12* (2013.01); *Y10T 436/143333* (2015.01)

(58) Field of Classification Search
  USPC ....... 436/501, 94, 164, 165, 172; 422/82.05, 422/82.08, 82.09; 435/6.1, 7.1
  See application file for complete search history.

(56) References Cited

U.S. PATENT DOCUMENTS

| | | | |
|---|---|---|---|
| 5,319,575 | A | 6/1994 | Lilienfeld |
| 5,866,336 | A | 2/1999 | Nazarenko et al. |
| 6,280,960 | B1 | 8/2001 | Carr |
| 6,376,843 | B1 | 4/2002 | Palo |
| 6,388,746 | B1 | 5/2002 | Eriksson et al. |
| 6,388,788 | B1 | 5/2002 | Harris et al. |
| 6,400,487 | B1 | 6/2002 | Harris et al. |
| 6,403,338 | B1 | 6/2002 | Knapp et al. |
| 6,710,871 | B1 | 3/2004 | Goix |
| 6,782,297 | B2 | 8/2004 | Tabor |
| 6,856,391 | B2 | 2/2005 | Garab et al. |
| 6,927,401 | B1 | 8/2005 | Palo |
| 8,284,484 | B2 | 10/2012 | Hoult et al. |
| 8,680,485 | B2 * | 3/2014 | Tanabe ............... G01N 21/6458 250/459.1 |
| 9,068,944 | B2 | 6/2015 | Tanabe |
| 9,188,535 | B2 * | 11/2015 | Hanashi ............ G01N 15/1429 |
| 2001/0035954 | A1 | 11/2001 | Rahn et al. |
| 2002/0008211 | A1 | 1/2002 | Kask |
| 2002/0036775 | A1 | 3/2002 | Wolleschensky et al. |
| 2003/0036855 | A1 | 2/2003 | Harris et al. |
| 2003/0218746 | A1 | 11/2003 | Sampas |
| 2004/0022684 | A1 | 2/2004 | Heinze et al. |
| 2004/0051051 | A1 | 3/2004 | Kato et al. |
| 2004/0150880 | A1 | 8/2004 | Nakata et al. |
| 2005/0130122 | A1 | 6/2005 | Aravanis et al. |
| 2005/0260660 | A1 | 11/2005 | van Dongen et al. |
| 2006/0078998 | A1 | 4/2006 | Puskas et al. |
| 2006/0158721 | A1 | 7/2006 | Nakata et al. |
| 2006/0256338 | A1 | 11/2006 | Gratton et al. |
| 2008/0052009 | A1 | 2/2008 | Chiu et al. |
| 2008/0067133 | A1 | 3/2008 | Bryant et al. |
| 2008/0158561 | A1 | 7/2008 | Vacca et al. |
| 2009/0159812 | A1 | 6/2009 | Livingston |
| 2010/0033718 | A1 | 2/2010 | Tanaami |
| 2010/0177190 | A1 | 7/2010 | Chiang et al. |
| 2010/0202043 | A1 | 8/2010 | Ujike |
| 2013/0302906 | A1 * | 11/2013 | Tanabe ............... G01N 21/6452 436/172 |
| 2014/0134608 | A1 * | 5/2014 | Hanashi ............ G01N 21/6408 435/5 |
| 2015/0218628 | A1 * | 8/2015 | Hanashi ................ G01N 21/76 506/9 |

FOREIGN PATENT DOCUMENTS

| | | |
|---|---|---|
| EP | 2840381 A1 | 2/2015 |
| JP | 04337446 A | 11/1992 |
| JP | 2002-507762 A | 3/2002 |
| JP | 2002-318188 A | 10/2002 |
| JP | 2002-543414 A | 12/2002 |
| JP | 2004-506192 A | 2/2004 |
| JP | 2005-098876 A | 4/2005 |
| JP | 2005-099662 A | 4/2005 |
| JP | 2007-020565 A | 2/2007 |
| JP | 4023523 B | 12/2007 |
| JP | 2008-116440 A | 5/2008 |
| JP | 2008-523376 A | 7/2008 |
| JP | 2008-536093 A | 9/2008 |
| JP | 2008-292371 A | 12/2008 |
| JP | 2009-145242 A | 7/2009 |
| JP | 2009-281831 A | 12/2009 |
| JP | 2009-288161 A | 12/2009 |
| JP | 2010-190730 A | 9/2010 |
| JP | 2011-002415 A | 1/2011 |
| JP | 2011-508219 A | 3/2011 |
| WO | 98/16814 A1 | 4/1998 |
| WO | 99/47963 A | 9/1999 |
| WO | 00/66985 A1 | 11/2000 |
| WO | 00/71991 A1 | 11/2000 |
| WO | 02/12864 A1 | 2/2002 |
| WO | 2006/084283 A2 | 8/2006 |
| WO | 2007/010803 A1 | 1/2007 |
| WO | 2007/118209 A2 | 10/2007 |
| WO | 2007/147159 A2 | 12/2007 |
| WO | 2008/007580 A1 | 1/2008 |
| WO | 2008/080417 A1 | 7/2008 |
| WO | 2009/106322 A1 | 9/2009 |
| WO | 2009/117033 A2 | 9/2009 |
| WO | 2010/119098 A1 | 10/2010 |
| WO | 2011/108369 A1 | 9/2011 |
| WO | 2011/108370 A1 | 9/2011 |
| WO | 2011/108371 A1 | 9/2011 |
| WO | 2012/014778 A1 | 2/2012 |
| WO | 2012/039352 A1 | 3/2012 |
| WO | 2013/031309 A1 | 3/2013 |

OTHER PUBLICATIONS

Wennmalm et al., "Inverse-Fluorescence Cross-Correlation Spectroscopy," Analytical Chemistry, vol. 82, No. 13, Jul. 1, 2010, pp. 5646-5651 (6 pages).
Final Office Action dated Sep. 29, 2015, issued in U.S. Appl. No. 13/946,091 (23 pages).
Final Office Action dated Sep. 28, 2015, issued in U.S. Appl. No. 13/746,968 (24 pages).
Extended European Search Report dated Oct. 20, 2014, issued in related EP Application No. 12770835.2 (10 pages).
English tranlation of Written Opinion of International Application No. PCT/JP2013/056600 (Form PCT/ISA/237) mailed Jun. 18, 2013 with ISR (Form PCT/ISA/210) (5 pages).
U.S. Office Action dated Feb. 9, 2015, issued in U.S. Appl. No. 14/496,177 (7 pages).
Related co-pending U.S. Appl. No. 14/496,177, Sep. 25, 2014.
Related co-pending U.S. Appl. No. 14/162,142, Jan. 23, 2014.
With English translation of Chinese Office Action dated Dec. 2, 2015, issued in related Chinese Patent Application No. 201380020726.5.
Office Action dated Jan. 27, 2016, issued in Chinese Patent Application No. 201280041717.X, w/English translation.
Office Action dated Mar. 22, 2016, issued in Japanese Patent Application No. 2013-531130, w/English translation.
Office Action dated Jun. 1, 2015, issued in counterpart Chinese Patent Application No. 201280041717.X, w/English translation (26 pages).
Non-Final Office Action dated Aug. 4, 2015, issued in U.S. Appl. No. 14/162,142 (41 pages).
Supplementary European Search Report dated Apr. 23, 2015, issued in counterpart European application No. 12828640.8 (16 pages).
Park, Mira et al., "Counting the Number of Fluorophores Labeled in Biomolecules by Observing the Fluorescence-Intensity Transient of a Single Molecule", Bulletin of the Chemical Society of Japan, Aug. 30, 2005, vol. 78, No. 9, p. 1612-1618.
U.S. Office Action dated Apr. 2, 2013, issued in related U.S. Appl. No. 13/596,280 (7 pages).
Kask, Peet et al., "Two-Dimensional Fluorescence Intensity Distribution Analysis: Theory and Applications", Biophysical Journal, Apr. 2000, vol. 78, p. 1703-1713.

(56) References Cited

OTHER PUBLICATIONS

Chinese Office Action dated Aug. 13, 2013, issued in related Chinese application No. 201180011655.3; w/ English Translation (16 pages).
International Search Report dated Mar. 29, 2011, issued in related PCT/JP2011/053483.
International Preliminary Report on Patentability (PCT/IPEA/409) issued in related PCT/JP2011/053483.
Chinese Office Action dated Aug. 9, 2013, issued in related Chinese application No. 201180011640.7; w/ English Translation (16 pages).
International Search Report Mar. 29, 2011, issued in related PCT/JP2011/053482.
International Preliminary Report on Patentability (PCT/IPEA/409) issued in related PCT/JP2011/053482.
U.S. Office Action dated Jan. 3, 2013, issued in related U.S. Appl. No. 13/597,825 (5 pages).
Chinese Office Action dated Feb. 7, 2013, issued in related Chinese application No. 201180011644.5; w/ English Translation (19 pages).
Extended European Search Report dated Mar. 28, 2013, issued in related EP application No. 11750481.1.
International Search Report dated Mar. 29, 2011, issued in related PCT/JP2011/053481.
International Preliminary Report on Patentability (PCT/IPEA/409) issued in related PCT/JP2011/053481.
Goodwin, Peter et al., "Rapid Sizing of Individual Fluorescently Stained DNA Fragments by Flow Cytometry", Nucleic Acids Research, 1993, vol. 21, No. 4, p. 803-806.
Keller, Richard et al., "Single-Molecule Fluorescence Analysis in Solution", Applied Spectroscopy, 1996, vol. 50, No. 7, p. 12A-32A.
Lee, Yuan-Hsiang et al., "Laser-Induced Fluorescence Detection of a Single Molecule in a Capillary", Analytical Chemistry, Dec. 1, 1994, vol. 66, No. 23, p. 4142-4149.
Li, Haitao et al., "Ultrasensitive Coincidence Fluorescence Detection of Single DNA Molecules", Analytical Chemistry, Apr. 1, 2003, vol. 75, No. 7, p. 1664-1670.
Nie, Shuming et al., "Probing Individual Molecules with Confocal Fluorescence Microscopy", Science, Nov. 11, 1994, vol. 266, p. 1018-1021.
Tahari, Abdel. "Fluorescence Correlation Spectroscopy: Ultrasensitive Detection in Clear and Turbid Media", University of Illinois, 2006, p. 1-88.
Wu, Alan et al., "Development and Preliminary Clinical Validation of a High Sensitivity Assay for Cardiac Troponin Using a Capillary Flow (Single Molecule) Fluorescence Detector", Clinical Chemistry, 2006, vol. 52, No. 11, p. 2157-2159.
Itoh et al., "A New Method for Detection of Influenza Viruses by Single Particle-Recognition Based on the Principle of Fluorescence Correlation Spectroscopy", Chemistry and Biology, 2009, vol. 47, No. 12, p. 823-830.
Carlsson, K. et al., "Three-dimensional Microscopy Using a Confocal Laser Scanning Microscope", Optics Letters, Optical Society of America, Feb. 1985, vol. 10, No. 2, p. 53-55, XP007922413.
U.S. Office Acion dated Oct. 4, 2013, issued in related U.S. Appl. No. 13/596,243 (7 pages).
Japanese Office Action dated Dec. 18, 2012, issued in related JP application No. 2012-503060; w/ English Translation (6 pages).
International Search Report dated Apr. 16, 2013, issued in related PCT/JP2013/050025.
International Search Report dated Jun. 18, 2013, issued in related PCT/JP2013/056600.
International Search Report dated Nov. 29, 2011, issued in related PCT/JP2011/072939.
Kask, Peet et al. "Fluorescence-Intensity Distribution Analysis and its Application in Biomolecular Detection Technology", PNAS, Nov. 23, 1999, vol. 96, No. 24, p. 13756-13761.
Kinjo, M. "Single Molecule Detection by Fluorescence Correlation Spectroscopy", Proteins, Nucleic Acids and Enzymes, 1999, vol. 44, No. 9, p. 1431-1438.
Meyer-Almes, F. J. "A New Method for Use in Molecular Diagnostics and High Throughput Pharmaceutical Screening based on Fluorescence Correlation Spectroscopy", Nanoparticle Immunoassays, R. Ridger, edit, Springer, Berlin, 2000, p. 204-224.
Kato, N. et al., "A Single Molecule Analyzer that Enables New Analysis of DNA and Protein Interactions", Gene Medicine, 2002, vol. 6, No. 2, p. 271-277.
International Search Report dated May 7, 2013, issued in related PCT/JP2013/052110.
International Search Report dated Oct. 15, 2013, issued in related PCT/JP2013/068406.
International Search Report dated Jul. 24, 2012, issued in related PCT/JP2012/063139.
U.S. Notice of Allowance dated Mar. 27, 2013, issued in related U.S. Appl. No. 13/597,825 (8 pages).
Extended (Supplementary) European Search Report (EESR) dated May 27, 2016, issued European Patent Application No. 13849687.2. (6 pages).
Chinese Office Action dated Aug. 3, 2016, issued in related Chinese application No. 201280041717.X; with English Translation.
U.S. Non-Final Office Action dated Dec. 22, 2016, issued in related co-pending U.S. Appl. No. 15/151,524.

* cited by examiner

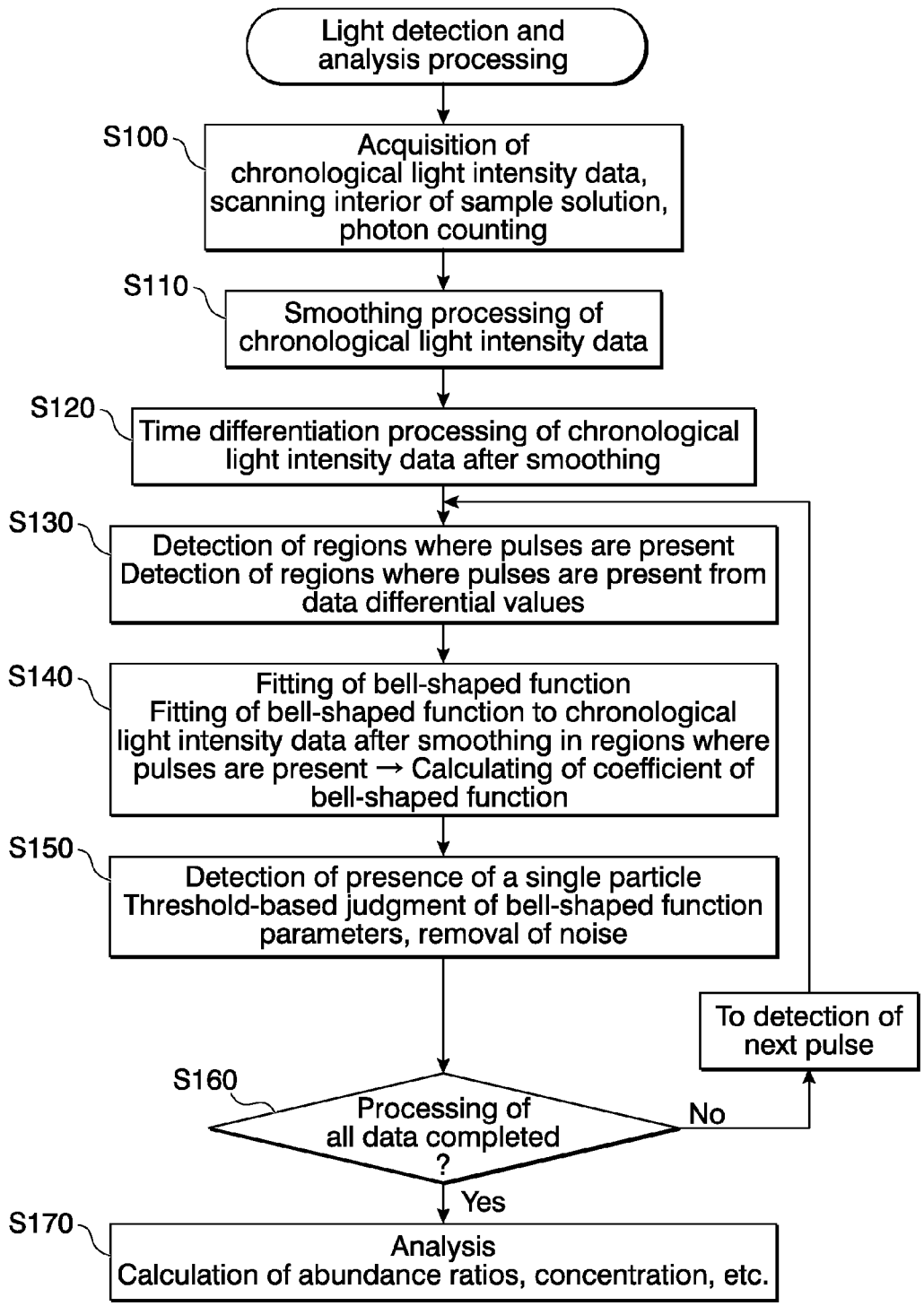

METHOD FOR DETECTING A TARGET PARTICLE

The present application claims priority on the basis of Japanese Patent Application No. 2012-095101, filed in Japan on Apr. 18, 2012, the contents of which are incorporated herein by reference. The present application is a U.S. continuation application based on the PCT International Patent Application, PCT/JP2013/052110, filed on Jan. 30, 2013; the contents of which are incorporated herein by reference.

BACKGROUND OF THE INVENTION

Field of the Invention

The present invention relates to a method for detecting a target particle using an optical system of a confocal microscope or multi-photon microscope and the like capable of detecting light from a microregion in a solution.

Description of the Related Art

Due to progress made in the field of optical measurement technology in recent years, it has become possible to detect and measure feint light at the level of a single photon or single fluorescent molecule using the optical system of a confocal microscope and ultra-high-sensitivity photodetection technology capable of performing photon counting (detecting individual photons). Therefore, various devices or methods have been proposed that detect interactions between molecules such as biomolecules or coupling and dissociation reactions between molecules using such feint light measurement technology. In particular, according to a method such as fluorescence correlation spectroscopy (FCS) or fluorescence intensity distribution analysis (FIDA) that uses a technology for measuring fluorescence of a microregion using the optical system of a confocal microscope and photocounting technology, the sample required for measurement is only required to be at an extremely low concentration and in an extremely small amount in comparison with that used in the past, and the amount used for a single measurement is roughly only several tens of microliters. In addition, measurement time is shortened considerably, and measurement of a duration on the order of several seconds for a single measurement is repeated several times. Furthermore, the aforementioned microregion refers to a confocal region where laser light of a microscope is focused, and is referred to as confocal volume. Moreover, one example of an aspect of FCS consists of calculating the value of an autocorrelation function of fluorescence intensity in a system in which detected light intensity decreases when non-luminescent particles dispersed in a solution in which a large amount of luminescent substances have been dissolved have entered a confocal volume, followed by calculating the translational diffusion time of the non-luminescent particles in the confocal volume along with the average value of the number of particles retained therein (inverse-FCS, or iFCS) (see, for example, International Patent Publication No. WO2010/119098).

More recently, an optical analysis technology (scanning molecule counting method) employing a novel approach has been proposed that individually detects luminescent particles (particles that emit light by fluorescence, phosphorescence, chemiluminescence, bioluminescence or light scattering and the like) crossing a photodetection region in a sample solution in the form of a microregion while moving the location of the microregion using an optical system capable of detecting light from a microregion in a solution, such as the optical system of a confocal microscope or multi-photon microscope (see, for example, International Publication No. WO 2011/108369; International Publication No. WO 2011/108370; and International Publication No. WO 2011/108371). More specifically, the scanning molecule counting method is a technique that enables counting of luminescent particles, or acquiring information relating to concentration or number density of luminescent particles in a sample solution, by detecting light emitted from the luminescent particles in a photodetection region to individually detect each of the luminescent particles in a sample solution while moving the location of the photodetection region of an optical system of a confocal microscope or multi-photon microscope in the sample solution using that optical system.

Since the photodetection mechanism per se of the scanning molecule counting method is composed so as to detect light from a photodetection region of a confocal microscope or multi-photon microscope in the same manner as in the case of optical analysis technologies such as FIDA, the amount of sample solution may also be an extremely small amount (such as roughly several tens of microliters) and only a short measurement time is required in the same manner as optical analysis technologies such as FIDA. On the other hand, the scanning molecule counting method differs from FIDA and the like, which requires statistical processing involving calculation of fluctuations in fluorescence intensity and the like, in that such statistical processing is not carried out. Consequently, optical analysis technology employing the scanning molecule counting method can be applied to sample solutions in which the number density or concentration of particles is considerably lower than the level required by optical analysis technologies such as FIDA. In other words, by detecting a target particle (an observation target particle) in a sample solution labeled with a luminescent probe using the scanning molecule counting method, the status or properties of the target particle can be detected and analyzed even in the case the concentration or number density of the target particles in the sample solution is extremely low (see, for example, International Publication No. WO 2012/014778).

SUMMARY OF THE INVENTION

As a result of conducting extensive studies to solve the aforementioned problems, the inventors of the present invention found that, in the scanning molecule counting method using the optical system of a confocal microscope or multi-photon microscope, if light containing substantially constant background light is detected in a photodetection region of the aforementioned optical system, although there is hardly any change in detected light intensity when particles sufficiently smaller than the photodetection region pass there through, when comparatively large particles pass there through, light is blocked by the particles and detected light intensity was found to decrease. Moreover, it was also found that, by detecting a decrease in background light (decrease in light intensity detected from a photodetection region) as a signal representing the presence of a target particle by using a non-luminescent particle having a size per molecule that is sufficiently smaller than the photodetection region as a labeling particle and labeling the target particle using a plurality of labeling particles per molecule, a labeling particle bound to the target particle can be distinguished from free labeling particles and detected.

Namely, the method for detecting target particles in one aspect of the present invention consists of that described in (1) to (12) below.

(1) The method for detecting a target particle in one aspect of the present invention is a method for detecting a non-luminescent target particle dispersed and randomly moving in a sample solution using an optical system of a confocal microscope or multi-photon microscope, comprising:

(a) preparing a sample solution containing target particles, and labeling particles of which the average outer diameter is less than 15% of the diameter of a photodetection region of the optical system, binding two or more molecules of the labeling particles per molecule of the target particles in the sample solution, and forming a non-luminescent complex of which the outer diameter is 15% or more of the diameter of the photodetection region; and, (b) calculating the number of molecules of the complex in the sample solution prepared in the (a), comprising:

moving the location of the photodetection region of the optical system in the sample solution, generating chronological light intensity data by detecting light containing substantially constant background light from the photodetection region while moving the location of the photodetection region of the optical system in the sample solution, individually detecting a decrease in light intensity in the chronological light intensity data that occurs when the complex has entered the photodetection region as a signal representing the presence of an individual complex, and counting the number of the complexes detected during movement of the location of the photodetection region by counting the number of signals representing the presence of the individually detected complexes.

(2) The method for detecting a target particle described in (1) above, wherein the outer diameter of the complex may be 35% or more of the diameter of the photodetection region.

(3) The method for detecting a target particle described in (1) or (2) above, wherein the target particle and the labeling particle bind specifically.

(4) The method for detecting a target particle described in any of (1) to (3) above, wherein the target particle is a nucleic acid.

(5) The method for detecting a target particle described in any of (1) to (4) above, wherein the background light is fluorescent light, phosphorescent light, chemiluminescent light, bioluminescent light, or scattered light generated by a substance dispersed in the sample solution.

(6) The method for detecting a target particle described in any of (1) to (4) above, wherein the background light is illumination light.

(7) The method for detecting a target particle described in any of (1) to (6) above, wherein, in the moving of the location of the photodetection region, the location of the photodetection region is moved at a speed faster than the diffusion movement speed of the complex.

(8) The method for detecting a target particle described in any of (1) to (7) above, wherein, in the moving of the location of the photodetection region, the location of the photodetection region in the sample solution is moved by altering the light path of the optical system.

(9) The method for detecting a target particle described in any of (1) to (8) above, wherein, in the individually detecting of a signal representing the presence of the complex, a single complex is judged to have entered the photodetection region when a signal has been detected having light intensity lower than a prescribed threshold value as determined from the intensity of the background light.

(10) The method for detecting a target particle described in any of (1) to (9) above, wherein, in the individually detecting of a signal representing the presence of the complex, the chronological light intensity data is smoothed, and a downwardly convex, bell-shaped pulsed signal, having intensity below that of a threshold value determined from the intensity of the background light in the smoothed chronological light intensity data, is detected as a signal representing the presence of the complex.

(11) The method for detecting a target particle described in any of (1) to (10) above, which further comprises determining the number density or concentration of the target particles in the sample solution based on the number of complexes detected and counted in the (b).

(12) The method for detecting a target particle described in any of (1) to (10) above, wherein, in the (b), the moving of the location of the photodetection region, the detecting of light from the photodetection region, and the detecting of a signal representing the presence of the complex may be repeated until the number of signals representing the presence of the complex reaches a predetermined number, and the concentration of the target particles in the sample solution may be determined based on the amount of time required for the number of signals representing the presence of the complex to reach the predetermined number.

BRIEF DESCRIPTION OF THE DRAWINGS

FIG. 3 is a drawing representing one aspect of the processing procedure of an inverse scanning molecule counting method in the form of a flow chart.

BEST MODE FOR CARRYING OUT THE INVENTION

Figure 1A:
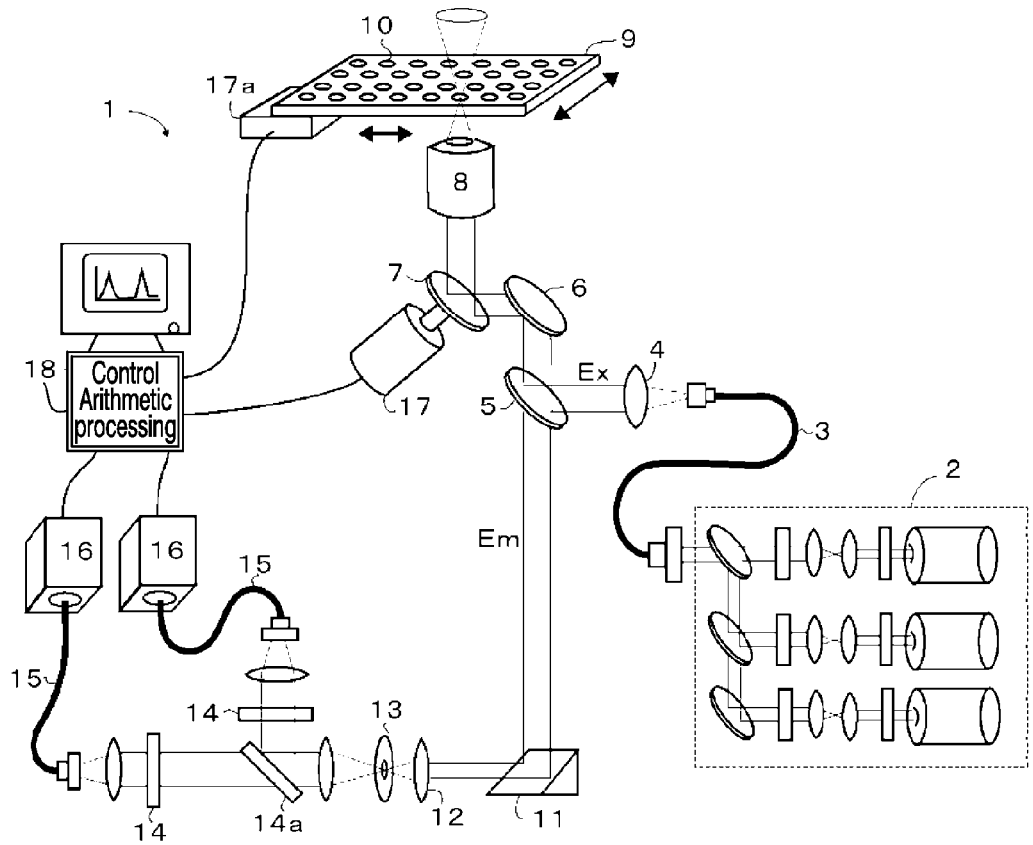
FIG. 1A is a schematic diagram of the internal structure of an optical analysis device for an inverse scanning molecule counting method.

The method for detecting a target particle of the present embodiment (to also be simply referred to as the "detection method of the present embodiment") is a method for detecting a non-luminescent particle dispersed and randomly moving in a sample solution by using an optical system of a confocal microscope or multi-photon microscope using an inverse scanning molecule counting method. The inverse scanning molecule counting method refers to a scanning molecule counting method that detects light containing substantially constant background light from a photodetection region of the aforementioned optical system, and detects the presence of a particle passing through the aforementioned photodetection region by using a decrease in light intensity detected from the aforementioned photodetection region as an indicator.

In the ordinary scanning molecule counting method described in references (International Publication No. WO 2011/108369; International Publication No. WO 2011/108370; International Publication No. WO 2011/108371; and International Publication No. WO 2012/014778), the particle targeted for observation is a luminescent particle, and a non-luminescent particle is unable to be detected. Thus, in the case of using a particle that inherently does not emit light as an observation target, it is necessary to impart a luminescent label such as a fluorescent label to the particle. However, it may be difficult to impart a luminescent label depending on the particular particle, or imparting of a luminescent label may cause degeneration of the particle. In addition, in the case of a system in which light released by the particle is identified as a signal representing the particle, when an increase in the value thereof in terms of light intensity data occurs caused by stray light, scattered light or electrical noise from a photodetector, the increase in that value may be erroneously identified as the signal of a luminescent particle.

On the other hand, in the case of measuring light with the optical system of a microscope in general, there is less susceptibility to the effects of Raman scattering attributable to stray light or water when the level of background light is high. In addition, in the case of the optical system of a confocal microscope or multi-photon microscope, since resolution in the direction of the optical axis is higher than that of ordinary light microscopes, a decrease in light intensity is observed from the confocal volume when a non-luminescent particle passes through the confocal volume. In other words, as a result of carrying out measurements using the inverse scanning molecule counting method in the presence of adequate background light, a target particle can be measured in an environment in which the effects of Raman scattering attributable to stray light or water have been reduced. In addition, a target particle is not required to be labeled with a luminescent probe and the like.

In the present embodiment, a "photodetection region" of the optical system of a confocal microscope or multi-photon microscope refers to a microregion in which light is detected in those microscopes, and in the case illumination light is imparted from an object lens, the region where that illumination light is focused corresponds to a microregion. Furthermore, this microregion is defined by the positional relationship between the object lens and pinhole in a confocal microscope in particular.

In the present embodiment, "a particle dispersed and moving randomly in a solution" refer to a particle such as an atom, a molecule or an aggregate thereof dispersed or dissolved in a solution (and may be a particle that emits light or a particle that does not emit light) that moves about freely by Brownian movement in a solution without being immobilized on a substrate and the like.

In the inverse scanning molecule counting method, light is successively detected while moving the location of a photodetection region in a sample solution, or in other words, while scanning the sample solution by photodetection regions, in the same manner as the scanning molecule counting method. In this configuration, in the case substantially constant background light is contained in the light from the photodetection region, when "a non-luminescent particle having a certain size relative to the photodetection region" has entered the photodetection region, or when the photodetection region that moves in a sample solution contains the aforementioned non-luminescent particle, light intensity or the amount of background light that reaches a photodetector from the photodetection region decreases due to the presence of the aforementioned particle. In this manner, in the inverse scanning molecule counting method, a decrease in the light intensity or amount of this background light is individually detected as a signal of the aforementioned non-luminescent particle in successively detected light. As a result, the presence of a particle is individually and successively detected, and various information relating to the status of the particle in solution is acquired. Furthermore, in the present embodiment, a "particle signal" refers to a signal that represents the presence of the aforementioned particle unless specifically indicated otherwise.

First, an explanation is provided of the inverse scanning molecule counting method.

<Configuration of Optical Analysis Device for Inverse Scanning Molecule Counting Method>

As schematically exemplified in FIG. 1A, the inverse scanning molecule counting method can be realized by an optical analysis device having a basic configuration composed by combining the optical system of a confocal microscope capable of performing FCS or FIDA and the like and a photodetector. With reference to FIG. 1A, an optical analysis device 1 is composed of optical system components 2 to 17, and a computer 18 for controlling the operation of each unit of the optical system components and acquiring and analyzing data. The optical system of the optical analysis device 1 may be composed in the same manner as the optical system of an ordinary confocal microscope. In the optical system of the optical analysis device 1, laser light (Ex) that has been radiated from a light source 2 and propagated through a single-mode optic fiber 3 is radiated in the form of light that emanates at an angle determined according to a characteristic numerical aperture (NA) at the outgoing end of the fiber, and the laser light is converted to parallel light by a collimator 4 and reflected by a dichroic mirror 5 and reflecting mirrors 6 and 7, after which it enters an object lens 8. A microplate 9, in which are typically arranged sample containers or wells 10 into which are dispensed one to several tens of microliters of a sample solution, is arranged above the object lens 8. Laser light emitted from the object lens 8 is focused on the sample solution in the sample containers or wells 10, forming a region of high light intensity (excitation region). An arbitrary luminescent substance that generates background light may also be dispersed or dissolved in the sample solution in addition to a non-luminescent particle such as a particle targeted for observation in the form of a non-luminescent particle (a target particle in the method of the present embodiment). In this case, when the non-luminescent particle does not enter the excitation region, the luminescent substance is excited and substantially constant light is released that becomes background light, while the background light decreases when the non-luminescent particle enters the excitation region.

Figure 1B:
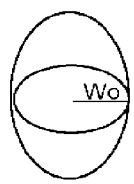
FIG. 1B is a schematic diagram of a confocal volume (photodetection region of a confocal microscope).
Figure 1C:
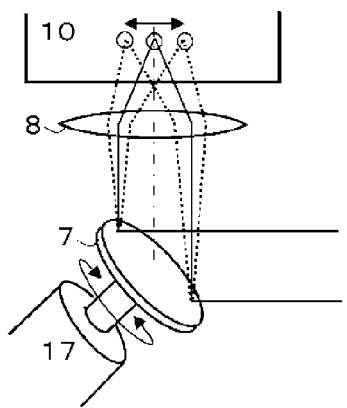
FIG. 1C is a schematic drawing of a mechanism for moving the location of a photodetection region in a sample solution by changing the orientation of a mirror 7.

In this manner, the light (Em) released from the excitation region passes through the object lens 8 and the dichroic mirror 5, is reflected by a mirror 11, is concentrated by a condenser lens 12 after which it passes through a pinhole 13 followed by passing through a barrier filter 14 (here, only light components of a specific wavelength band are selected), the released light is then introduced into a multi-mode optic fiber 15 and reaches a photodetector 16, and after being converted to a chronological electrical signal, is input to the computer 18 where processing is carried out for detecting a single particle by an aspect to be subsequently explained (a particle demonstrating behavior as a single particle, and in the detection method of the present invention, a complex consisting of a target particle and labeling particle is included in addition to free target particles and free labeling particles). Furthermore, as is known among persons skilled in the art, the pinhole 13 is arranged at a location conjugate to the focal position of the object lens 8 in the aforementioned configuration. As a result, only light emitted from the focused region of the laser light as schematically shown in FIG. 1B, namely light emitted from the excitation region, passes through the pinhole 13, while light from a location other than the excitation region is blocked. The focused region of the laser light exemplified in FIG. 1B is normally a photodetection region in the present optical analysis device having an effective volume of about 1 fL to 10 fL and is referred to as confocal volume (and typically has a Gaussian distribution in which light intensity reaches a peak in the center of the region, and the effective volume is the volume of a roughly ellipsoidal shape in which the boundary of light intensity is a plane defined as $1/e^2$). In addition, in the present embodiment, since a decrease in the amount of light is detected by the presence of a single particle in background light composed of feint light from roughly several fluorescent dye molecules, an ultra-high-sensitivity photodetector capable of use in photon counting may be used for the photodetector 16. In the case of detecting light by photon counting, measurement of light intensity is carried out by an aspect in which the number of photons arriving at the photodetector is successively counted at prescribed unit time intervals (bin time) over a prescribed amount of time. Thus, in this case, chronological light intensity data is chronological photon count data. In addition, the stage of the microscope (not shown) may be provided with a stage position adjustment device 17a for moving the location of the microplate 9 in the horizontal direction in order to change the well 10 to be observed. Operation of the stage position adjustment device 17a is controlled by the computer 18. As a result of employing this configuration, measurements can be carried out rapidly even in the case of multiple specimens.

Figure 1D:
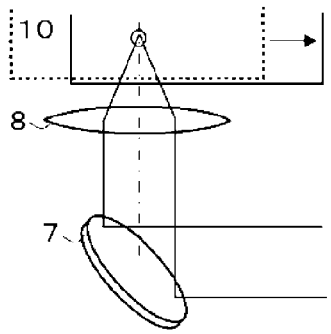
FIG. 1D is a schematic diagram of a mechanism for moving the location of a photodetection region in a sample solution by moving the location of a microplate in the horizontal direction.

Moreover, in the optical system of the aforementioned optical analysis device, a mechanism is provided for scanning the sample solution by photodetection regions, namely for moving the location of the focused region, namely the photodetection region, in the sample solution. A mirror light deflector 17 that changes the orientation of the reflecting mirror 7, for example, may be employed as a mechanism for moving the location of the photodetection region in this manner as schematically exemplified in FIG. 10 (system for moving the relative location of the photodetection region). This mirror light deflector 17 may be composed in the same manner as a galvanometer mirror device provided in ordinary laser scanning optical microscopes. Alternatively, as an example of a different aspect, a stage position adjustment device 17a may be operated so as to move the relative location of the photodetection region in the sample solution by moving the location of the container 10 (microplate 9) injected with sample solution in the horizontal direction (system for moving the relative location of the sample solution) as exemplified in FIG. 1D. In the case of either system, the mirror light deflector 17 or the stage position adjustment device 17a is driven in coordination with light detection by the photodetector 16 under the control of the computer 18 so as to achieve a desired movement pattern for the location of the photodetection region. The movement locus of the location of the photodetection region is arbitrarily selected from among a circular, oval, rectangular, linear and curved locus or a combination thereof (or various movement patterns programmed in the computer 18 can be selected). In addition, movement of the relative location of the photodetection region may also be carried out while moving the location of the sample solution by combining a system for moving the absolute location of the photodetection region and a system for moving the absolute location of the sample solution. In this case, repeated detection of the same single particle, caused by the photodetection region passing through the same region within a short period of time, is avoided. Alternatively, a system for moving the absolute location of the photodetection region may also be used to improve signal accuracy by intentionally causing the same region to repeatedly pass through the photodetection region so that the same single particle is periodically detected over a plurality of times. In this case, after moving the absolute location of the photodetection region over a prescribed amount of time, the location of the sample solution is moved intermittently and the same single particle is detected repeatedly at different locations in the sample solution with the intention of increasing the number of single particles detected. Furthermore, although not shown in the drawings, the location of the photodetection region may be moved in the vertical direction by moving the object lens 8 or stage up and down to enable the locus of the location of the photodetection region to be deployed three-dimensionally in the sample solution.

In the case a luminescent substance generating background light emits light by multi-photon absorption, the aforementioned optical system is used in the form of a multi-photon microscope. In that case, since light is only released in the focused region of excitation light (photodetection region), the pinhole 13 may be omitted. In addition, in the case a luminescent substance generating background light emits light by a chemiluminescent or bioluminescent phenomenon without relying on excitation light, the optical system components 2 to 5 for generating excitation light may also be omitted. In the case a luminescent substance generating background light emits light by phosphorescence or light scattering, the aforementioned optical system of a confocal microscope is used as is. Moreover, in the device 1, a plurality of the excitation light sources 2 are provided as shown in FIG. 1A, and these are composed so as allow the wavelength of the excitation light to be suitably selected according to the excitation wavelength of the luminescent substance. Similarly, a plurality of the photodetectors 16 is also provided, and may be made to each detect light corresponding to the wavelength of background light. Moreover, the background light may be imparted by illumination light. In that case, the sample solution is illuminated by transillumination (which may also be Koehler illumination) from above the object lens.

<Principle of Optical Analysis Technology of Scanning Molecule Counting Method>

In plain terms, the inverse scanning molecule counting method enables the detection of the presence of an individual particle and acquisition of information relating to the number or concentration thereof in a sample solution by a type of scanning molecule counting method for detecting the shadow of a single particle, or in other words, is an aspect in which a decrease in background light, when the location of a photodetection region in a sample solution is moved and a single non-luminescent particle is contained in that photodetection region, is detected as a signal corresponding to that single particle.

Figure 2A:
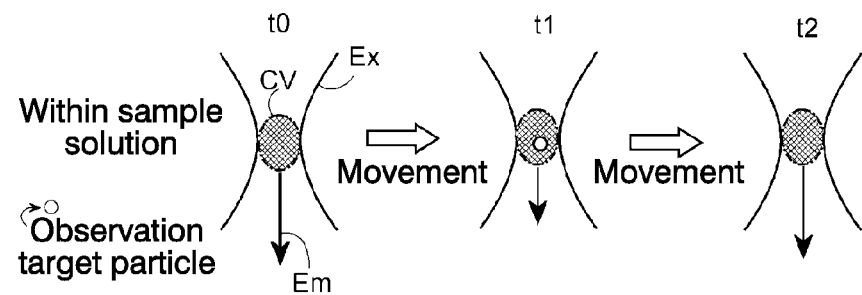
FIG. 2A is a schematic diagram for explaining a principle used to detect the presence of a single non-luminescent particle with an inverse scanning molecule counting method and a schematic diagram of chronological changes in measured light intensity.
Figure 2B:
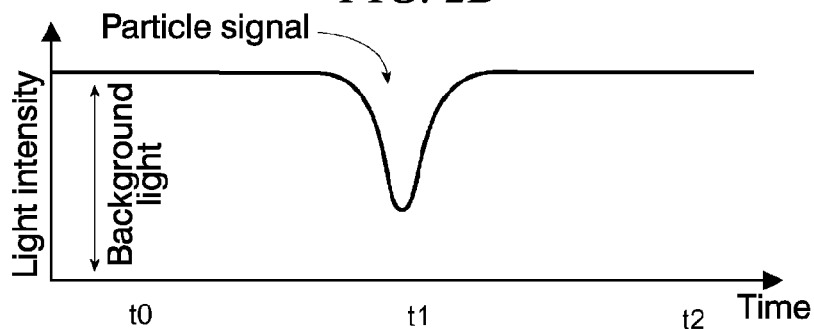
FIG. 2B is a schematic diagram for explaining a principle used to detect the presence of a single non-luminescent particle with an inverse scanning molecule counting method and a schematic diagram of chronological changes in measured light intensity.

More specifically, similar to the ordinary scanning molecule counting method, photodetection is carried out by changing the light path by driving a mechanism (mirror light defector 17) while moving the location of the photodetection region, or by moving the location of a container 10 into which a sample solution has been injected (microplate 9) in the horizontal direction, and detecting light while moving the location of the photodetection region CV in the sample solution, namely while scanning the interior of the sample solution with the photodetection region CV, as is schematically depicted in FIG. 2A. As was previously mentioned, since luminescent substances are dispersed in the sample solution and a large number of luminescent substances are present in the photodetection region CV, light from these luminescent substances is basically detected roughly uniformly during movement of the photodetection region CV (from time t0 to t2 in FIG. 2A). However, when the photodetection region CV passes through a region where a single non-luminescent particle is present during movement thereof (time t1), the total amount of light released by the luminescent substances decreases since the volume of the region where the luminescent substances are present decreases, and as depicted in FIG. 2B, a significant decrease in light intensity (Em) in the shape of a bell-shaped pulse appears in chronological light intensity data. Thus, movement of the location of the photodetection region CV and light detection are carried out as previously described, and a significant pulse-shaped decrease in light intensity, namely an individual signal representing the presence of a single particle, is detected as exemplified in FIG. 2B during the time of the appearance thereof. As a result, by individually detecting a single particle and counting the number thereof, the number of single particles present in a measured region, or information relating to the concentration or number density thereof, can be acquired.

Figure 2C:
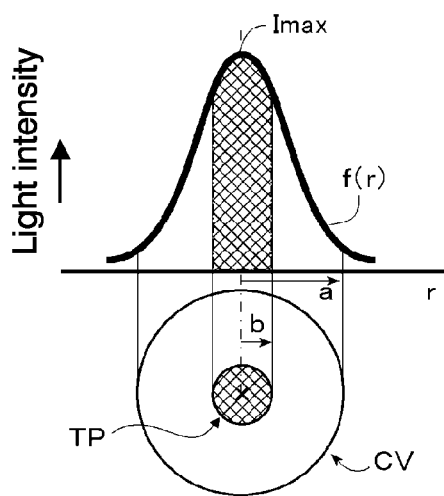
FIG. 2C is a drawing for explaining the principle of a decrease in the amount of detected light when a single non-luminescent particle has entered a photodetection region.

In the case of a decrease in light intensity as previously described, the decrease can be estimated from the relationship between the diameter of the single non-luminescent particle and the diameter of the photodetection region. With reference to FIG. 2C, the distribution of light intensity in the photodetection region has a maximum intensity Imax at the center thereof and depicts a bell-shaped profile f(r) in which light intensity decreases moving in the directions of radius r as is indicated with the solid line in FIG. 2C. Thus, the total amount of light a released from the photodetection region when a non-luminescent particle is not present in the photodetection region is given by equation (1) by using the radius a of the photodetection region when f(r) is approximately zero.

$$\alpha = 4\pi \int r^2 f(r) dr \text{ (integration interval: 0 to } a) \quad (1)$$

On the other hand, when a single non-luminescent particle of radius b has entered the photodetection region and is located at the center of the photodetection region as in the lower part of FIG. 2C, luminescent substances in that region are excluded. Accordingly, the amount of light decreases corresponding to the region indicated with diagonal lines in the upper part of FIG. 2C. The amount of light corresponding to the excluded luminescent substances, namely the amount of decrease β, is given by equation (2).

$$\beta = 4\pi \int r^2 f(r) dr \text{ (integration interval: 0 to } b) \quad (2)$$

Thus, the ratio of the decrease in light intensity can be estimated from β/α.

Here, f(r) is a Gaussian function, and when α=1 and a=1, f(r) can be represented by equation (3).

$$f(r) = 0.684 \exp(-2r^2) \quad (3)$$

Figure 2D:
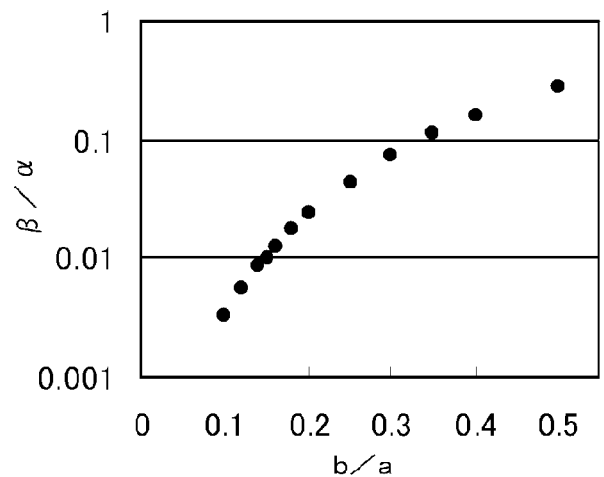
FIG. 2D is a drawing indicating the relationship between the ratio between the diameters of a photodetection region and a single particle and the ratio of a decrease in an amount of detected light.

FIG. 2D is a graph in which the ratio β/α of the decrease in light intensity is plotted versus radius ratio b/a using formula (3). With reference to FIG. 2D, since the fluctuation rate of background light is typically about 1%, and a signal cannot be detected if the ratio of a decrease in light intensity attributable to a single particle is 1% or less, the ratio b/a of the radius of a single particle to the radius of the photodetection region should be 0.15 or more. In addition, in the case of making the ratio of a decrease in light intensity attributable to a single particle to be 10% or more, the ratio b/a of the radius of a single particle able to be detected to the radius of the photodetection region becomes 0.35.

Furthermore, in the case the single particle to be observed is a quencher or acceptor of fluorescent energy transfer, since the signal particle absorbs surrounding light (over a range of, for example, 10 nm), the detectable single particle radius can be decreased beyond the previously exemplified radius.

<Processing Procedure of Inverse Scanning Molecule Counting Method>

In the inverse scanning molecule counting method, the light intensity of a sample solution containing a particle targeted for observation is measured and then analyzed. FIG.

3 indicates one aspect of the processing procedure of the inverse scanning molecule counting method in the form of a flow chart.

(Measurement of Light Intensity of Sample Solution: S100 of FIG. 3)

Measurement of light intensity by optical analysis according to the inverse scanning molecule counting method is carried out in the same manner as the measurement process used to measure light intensity by FCS or FIDA with the exception of moving the location of the photodetection region in a sample solution by driving the mirror light deflector 17 or the stage position adjustment device 17a during measurement. During operational processing, sample solution is typically injected into the wells 10 of the microplate 9, and after placing the microplate 9 on the microscope stage, when a user inputs instructions for starting measurement to the computer 18, the computer 18 initiates radiation of excitation light and measurement of light intensity in a photodetection region in the sample solution in accordance with a program (consisting of a procedure for moving the location of the photodetection region in the sample solution and a procedure for generating chronological light intensity data by detecting light from the photodetection region during movement of the location of the photodetection region) stored in a memory device (not shown). During the time this measurement is being carried out, the mirror light deflector 17 or the stage position adjustment device 17a drives the mirror 7 (galvanometer mirror) or the microplate 9 on the microscope stage under the control of a processing operation in accordance with the program of the computer 18, and the location of the photodetection region is moved in the wells 10. At the same time, the photodetector 16 converts successively detected light to electrical signals and transmits those signals to the computer 18, where the computer 18 generates and stores chronological light intensity data from the transmitted signals by an arbitrary means. Furthermore, since the photodetector 16 is typically an ultra-high-sensitivity photodetector capable of detecting the arrival of a single photon, in the case light detection is carried out by photon counting, the chronological light intensity data may be in the form chronological photon count data.

The movement speed of the location of the photodetection region during measurement of light intensity may be an arbitrary speed, and for example, may be a prescribed speed set experimentally or so as to comply with the analysis objective. In the case of acquiring information relating to particle number density or concentration based on the number of single particles detected, since the region through which the photodetection region passes is required to have a certain size or volume, the location of the photodetection region is moved by an aspect that allows movement distance to be determined. Furthermore, since the presence of a proportional relationship between elapsed time during measurement and movement distance of the location of the photodetection region facilitates interpretation of measurement results, movement speed may be basically made to be a constant speed, although not limited thereto.

Figure 4A:
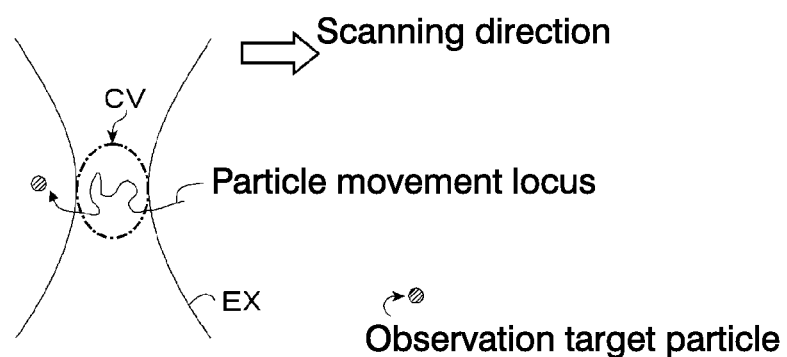
FIG. 4A is a model drawing representing an aspect of particle movement in the case of a single particle crossing a photodetection region while demonstrating Brownian movement and in the case of a particle crossing a photodetection region as a result of moving the location of the photodetection region in a sample solution at a speed faster than the diffusion movement speed of the single particle.
Figure 4B:
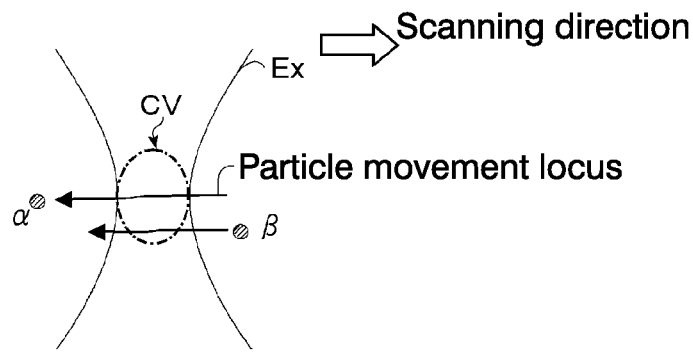
FIG. 4B is a model drawing representing an aspect of particle movement in the case of a single particle crossing a photodetection region while demonstrating Brownian movement and in the case of a particle crossing a photodetection region as a result of moving the location of the photodetection region in a sample solution at a speed faster than the diffusion movement speed of the single particle.

However, with respect to movement speed of the location of the photodetection region, in order to individually detect single particles from measured chronological light intensity data or accurately and quantitatively carry out photon counting of the number of single particles, the movement speed may be set to value that is faster than the random movement speed of the single particles, namely the movement speed attributable to Brownian movement. Since an observation target particle in the inverse scanning molecule counting method is a particle that is dispersed or dissolved in a solution and randomly move about freely therein, their locations based on Brownian movement move over time. Thus, in the case movement speed of the location of the photodetection region is slower than movement attributable to Brownian movement, a particle randomly moves through the region as schematically depicted in FIG. 4A. As a result, light intensity changes randomly (and as was previously mentioned, excitation light intensity in a photodetection region has its peak in the center of the region and then decreases moving to either side), thereby making it difficult to specify significant changes in light intensity corresponding to an individual single particle. Therefore, the movement speed of the location of the photodetection region may be set to be faster than the average movement speed attributable to Brownian movement (diffusion movement speed) so that a particle crosses the photodetection region in nearly a straight line as depicted in FIG. 4B, and as a result thereof, a profile of the change in light intensity corresponding to an individual single particle becomes nearly uniform in the chronological light intensity data as exemplified in the upper graph of FIG. 4C (in the case a single particle crosses the photodetection region in nearly a straight line, the profile of changes in light intensity is roughly the same as the profile obtained by inverting the distribution of excitation light intensity), and the correspondence between an individual particle and light intensity can be easily determined.

In addition, in the inverse scanning molecule counting method, a single particle is individually detected by detecting a decrease in background light due to the presence of a single particle when the photodetection region passes through the location where that single particle is present. However, in the case a single particle moves randomly in a solution due to Brownian movement and enters and leaves the photodetection region multiple times, a signal corresponding to the presence thereof ends up being detected a plurality of times from one single particle, thereby making it difficult to create a correspondence between the detected signal and the presence of one single particle. Therefore, as was previously described, the movement speed of the photodetection region is set to be faster than the diffusion movement speed of a single particle, and as a result thereof, a single signal (representing the presence of a single particle) can be made to correspond to a single particle.

More specifically, a time Δt required for a particle having a diffusion coefficient D to pass through a photodetection region (confocal volume) having a radius Wo by Brownian movement can be expressed with equation (5) from the following relational expression (4) of mean square displacement.

$$(2Wo)^2 = 6D \cdot \Delta t \tag{4}$$

$$\Delta t = (2Wo)^2/6D \tag{5}$$

Thus, the speed Vdif (diffusion movement speed) at which particles move by Brownian movement (diffusion movement speed) can generally be expressed as indicated below.

$$V\text{dif} = 2Wo/\Delta t = 3D/Wo \tag{6}$$

Therefore, the movement speed during movement of the location of the photodetection region is set to a value that is sufficiently faster than Vdif by referring thereto. For example, in the case the diffusion coefficient D of an observation target particle is predicted to be about $2.0 \times 10^{-10}$ m²/s and Wo is about 0.62 μm, Vdif becomes $1.0 \times 10^{-3}$ m/s. Accordingly, the movement speed of the location of the photodetection region is set to a value about 10 times greater than that, 15 mm/s etc. Furthermore, in the case the diffusion coefficient of an observation target particle is unknown, a movement speed of the location of the photodetection region may be determined by repeatedly carrying out preliminary experiments in order to find those conditions under which the prolife of changes in light intensity become the predicted profile (and typically, a prolife that is roughly the same as the excitation light distribution) by trying various settings for the movement speed of the location of the photodetection region.

(Analysis of Light Intensity)

Once chronological light intensity data has been obtained according to the aforementioned processing, various types of analyses are carried out, such as detection of the signals of single particles, counting of single particles or calculation of concentration, by processing in the computer 18 in accordance with the program stored in a memory device.

A judgment as to whether or not a single particle has entered a photodetection region is made based on the shape of chronological light intensity data obtained according to the aforementioned processing. Typically, the intensity of background light is first measured followed by judging that one single particle has entered the photodetection region when a signal having light intensity lower than a prescribed threshold value is detected. More specifically, normally a signal representing the presence of a single particle appears as a downwardly convex bell-shaped pulsed signal having intensity below a certain degree of intensity in the chronological detection values of a photodetection region, namely light intensity data, while noise does not have a bell-shaped pulsed shape or appears as a signal of high intensity. Therefore, a configuration may be employed such that the intensity of background light is first measured followed by detecting a downwardly convex bell-shaped pulsed signal having an intensity below a prescribed threshold value as a signal representing the presence of a single particle. The "prescribed threshold value" can be set experimentally to a suitable value.

Moreover, light intensity obtained by an optical analysis device used in the inverse scanning molecule counting method is comparatively feint and increases or decreases slightly, and these slight increases or decreases in light intensity have a detrimental effect on detection accuracy of a signal representing the presence of a single particle. Therefore, downwardly convex bell-shaped pulsed signals having an intensity below that of a prescribed threshold value may be detected as a signal representing the presence of a single particle by smoothing the chronological light intensity data to obtain data that enables these slight increases and decreases in light intensity to be ignored, followed by measuring the intensity of background light in this smoothed chronological light intensity data.

In the inverse scanning molecule counting method, the number of signal particles contained in a photodetection region is counted by counting the number of signals (particle counting). In this case, information relating to the number density or concentration of single particles identified in a sample solution is obtained by combining the number of detected single particles and the amount of movement of the location of the photodetection region. More specifically, the ratio of the number densities or concentrations of a plurality of sample solutions, or the ratio of the relative number density or concentration relative to a standard sample solution serving as a reference for concentration or number density, for example, is calculated, or the absolute value of number density or concentration may be determined using the ratio of number density or concentration relative to a standard sample solution serving as a reference for concentration or number density. Alternatively, the number density or concentration of a single particle can be calculated in detail by specifying the total volume of the movement locus of the location of the photodetection region by moving the location of the photodetection region at a prescribed speed, for example, according to an arbitrary technique.

The following provides a more detailed explanation thereof.

(i) Individual Detection of a Single Particle Signal

Figure 4C:
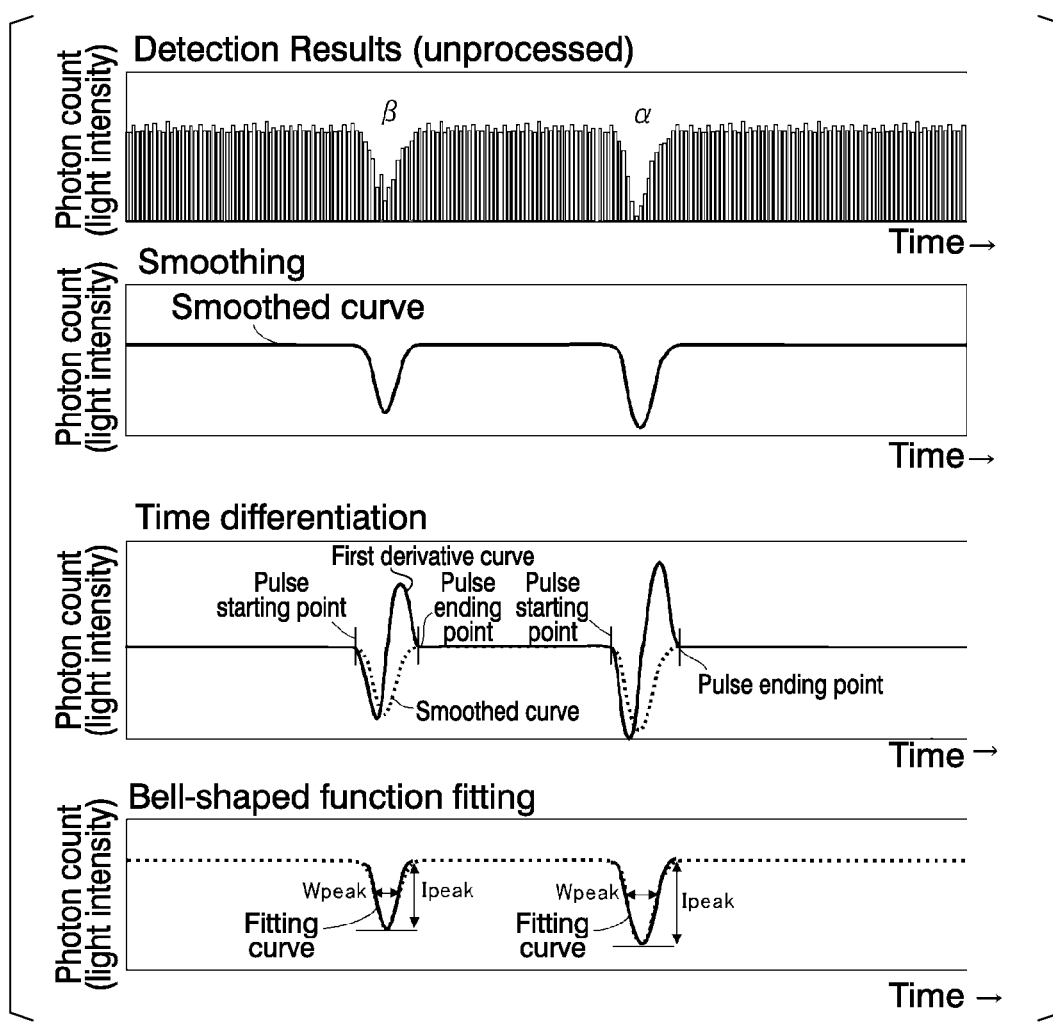
FIG. 4C is a drawing for explaining an example of a process used to process detection signals in a processing procedure for detecting the presence of a single particle from calculated chronological light intensity data (chronological changes in a photon count) in accordance with an inverse scanning molecule counting method.

In chronological light intensity data, in the case the movement locus when a single observation target particle passes through a photodetection region is roughly linear in the manner shown in FIG. 4B, the change in light intensity in the signal corresponding to that particle has a downwardly convex roughly bell-shaped profile that reflects the distribution of light intensity in the photodetection region (determined according to the optical system) (refer to the upper graph of FIG. 4C). Thus, in the scanning molecule counting method, when a time width, during which a decrease in light intensity that is below a threshold value suitably set by measuring background light continues, is within a prescribed range, a signal having a profile in which the light intensity thereof decreases is basically judged to correspond to the passage of a single particle through the photodetection region, resulting in detection of a single particle. A signal in which a time width, during which a decrease in light intensity that is below a threshold value continues, is not within prescribed range, that signal may be judged to be a signal representing noise or an artifact. In addition, the distribution of light intensity of a photodetection region can be assumed to be represented by a downwardly convex Gaussian distribution in the form of equation (7) from background light Ibg.

$$I = Ibg - A \cdot \exp(-2t^2/a^2) \quad (7)$$

When an intensity A and a width a, calculated by fitting equation (7) to a profile of a significant decrease in light intensity (profile that can be clearly determined to not constitute a fluctuation in background light), are within prescribed ranges, that profile of light intensity may be judged to correspond to the passage of a single particle through the photodetection region, thereby resulting in detection of a single particle.

Signals in which the intensity A and width a are outside prescribed ranges may be judged to be signals representing noise or artifacts, and may be ignored in subsequent analyses and the like.

In one example of a processing method for carrying out batch detection of single particles from chronological light intensity data, smoothing processing is first carried out on the chronological light intensity data (data indicated as "Detection result (unprocessed)" in the top graph of FIG. 4C) to obtain smoothed data (S110 in FIG. 3, indicated by "Smoothing" in the second graph from the top in FIG. 4C). Although slight increases or decreases occur in light emitted from luminescent substances since that light is detected on the basis of probability and the light intensity thereof is comparatively feint, these slight increases or decreases (fluctuations) in light intensity have a detrimental effect on the detection accuracy of a signal representing the presence of a single particle. Smoothing processing enables these slight increases or decreases in the data to be ignored. Smoothing processing is carried out by, for example, the moving average method. Furthermore, parameters used when carrying out smoothing processing, such as the number of data points averaged at one time, or the number of times movement is averaged in the case of the moving average method, are suitably set corresponding to the movement speed of the location of the photodetection region when acquiring optical signal data (scanning speed) and bin time.

Next, in order to detect a time region (pulse region) in which a significant pulsed signal (to be simply referred to as a "pulsed signal") is present in chronological optical intensity data following smoothing processing, a first derivative is calculated for the time of the chronological optical intensity data following smoothing processing (S120). Since the change in the value of the time derivative of chronological optical intensity data increases at the inflection point of the signal value as exemplified by "Time differentiation" in the second graph from the bottom in FIG. 4C, the starting point and ending point of a significant signal can be advantageously determined by referring to this time derivative.

Subsequently, a significant pulsed signal is successively detected in the chronological optical intensity data, and a judgment is made as to whether or not the detected peak signal is a signal corresponding to a single particle. More specifically, the starting point and ending point of a single pulsed signal are searched for and determined by successively referring to time derivatives in chronological time derivative data of chronological light intensity data to specify a pulse region (S130). Once a single pulse region has been specified, a downwardly convex bell-shaped function is fit to the smoothed chronological light intensity data in that pulse region ("Bell-shaped function fitting" in the bottom graph of FIG. 4C), followed by calculation of parameters such as pulse peak intensity Ipeak of the bell-shaped function (maximum amount of decrease from background light), pulse width (half width at maximum) Wpeak, and correlation coefficient (of the least squares method) during fitting (S140). Furthermore, although the bell-shaped function subjected to fitting is typically a Gaussian function, it may also be a Lorentzian function. A judgment is then made as to whether or not the calculated bell-shaped function parameters are within a presumed range for the parameters of a bell-shaped profile depicted by a pulsed signal detected when a single luminescent particle has passed through a photodetection region, namely whether or not pulse peak intensity, peak width and correlation coefficient are each within a prescribed range (S150). For example, a judgment is made as to whether or not the conditions indicated below are satisfied.

20 μs<pulse width<400 μs

Peak intensity>4.0(pc/10 μs)

Correlation coefficient>0.95 (A)

A signal for which the calculated bell-shaped function parameters are within the presumed ranges for a signal corresponding to a single particle is judged to be a signal corresponding to a single particle. On the other hand, a pulsed signal for which the calculated bell-shaped function parameters are not within the presumed ranges is ignored as noise.

Searching and judgment carried out on pulsed signals in the aforementioned S130 to S150 are carried out repeatedly over the entire range of chronological light intensity data (S160). Furthermore, processing for individually detecting signals of luminescent particles from chronological light intensity data is not limited to the aforementioned procedure, but rather may be carried out according to an arbitrary technique.

(ii) Determination of Particle Concentration

Moreover, the number of particles may be determined by counting the number of signals detected corresponding to single particles (particle counting). In addition, if the total volume of the region through which the photodetection region has passed is calculated using an arbitrary technique, the number density or concentration of particles in a sample solution is determined from that total volume and the number of particles (S170).

The total volume of the region through which the photodetection region has passed may be calculated theoretically based on the wavelength of excitation light or detection light, numerical aperture of the lens, and adjusted state of the optical system. In addition, total volume may also be determined for a solution having a known particle concentration (control solution) from the number of detected particles and the concentration of particles in the control solution by experimentally measuring light intensity as previously explained and carrying out detection and counting of particles under the same conditions as measurement of the sample solution to be tested. More specifically, when assuming the number of detected single particles N for a control solution having a particle concentration C, for example, then the total volume Vt of the traversed region of the photodetection region is given by the equation indicated below.

$$Vt=N/C \qquad (8)$$

In addition, a plurality of solutions having different concentrations of single particles may be provided for use as control solutions, measurements may be carried out on each control solution, and the average value of the calculated Vt may be used as the total volume Vt of the traversed region of the photodetection region. If Vt is given, then the concentration c of particles in a sample solution for which the result of counting single particles is n is given by the equation indicated below.

$$c=n/Vt \qquad (9)$$

Furthermore, the volume of a photodetection region and the total volume of a traversed photodetection region are not limited to the aforementioned method, but rather may also be given by an arbitrary method such as FCS or FIDA. In addition, the optical analysis device of the present embodiment may preliminarily store information on the relationship between concentration C and the number of particles N (Equation (6)) for various standard particles and for presumed photodetection region movement patterns in a memory device of the computer 18, and may be configured so that a device user is able to use that suitably stored relationship information when detecting single particles.

Thus, in the inverse scanning molecule counting method for individually detecting particles by scanning a sample solution with a photodetection region, use of the aforementioned processing procedure makes it possible to count the number of particles in the sample solution or determine the concentration thereof and the like.

(Single Particle Detection Processing for Detecting a Fixed Number of Signals)

In the aforementioned single particle detection processing, after measuring light over a certain set amount of time, a single particle signal is detected in the resulting light intensity data. In other words, the number of signals of single particles obtained during an arbitrary set measurement time is counted. In this case, when the particle concentration in a sample solution is unknown, in the case of measuring light intensity over a certain fixed measurement time, measurement time is set to a sufficiently long time in anticipation of the case of a low particle concentration. On the other hand, in the case particle concentration in the sample solution is high, measurement of light intensity is continued for a minimum amount of time required to determine concentration and other properties at an allowable or satisfactory accuracy. In addition, in the case the particle concentration in the sample solution is lower than the concentration presumed by the experimenter or the set measurement time is insufficient, the amount of error in the result increases. In this manner, the number of signals of detected single particles fluctuates according to the set duration of measurement time, and particularly when single particle concentration is low, variations in the single particle concentration as determined from the number of detected signals becomes large and accuracy can decrease.

Therefore, another aspect used to count particles consists of measuring the number of single particle signals until the number reaches an arbitrarily set number, and determining the concentration of single particles based on measurement time. Namely, another aspect of single particle detection processing consists of repeating measurement of light intensity while moving the photodetection region and detecting single particle signals until the number of signals reaches a predetermined number, measuring the amount of time required for the number of signals to reach the predetermined number, and determining particle concentration based on the amount of time required for the number of single particle signals to reach the predetermined number. According to this configuration, in the case the particle concentration in a sample solution is high, the amount of time required to measure light intensity is shortened, while in the case of the particle concentration in the sample solution is low, measurement of light intensity can be continued until the number particles at which a required level of accuracy is attained for the result (namely, particle concentration) is obtained. In other words, measurement time is optimized corresponding to the concentration of single particles.

By setting the predetermined number to be reached by the number of single particle signals to a number of particles at which a required level of accuracy is attained for the result, since the number of particles at which a required level of accuracy is attained for the result is reflected in the amount of time required for the number of single particle signals to reach a predetermined number, the concentration of particles determined based on that time can be expected to have an allowable or satisfactory level of accuracy. In other words, if the predetermined number is set to a number at which a required level of accuracy is attained for the result, fluctuations in the amount of time required to detect that predetermined number of single particles, or in an arbitrary result derived therefrom, are suppressed to a low level, thereby making it possible to achieve a satisfactory level of accuracy in the result.

(i) Basic Principle

There is a correlation between the value of particle concentration and the amount of time required for the number of signals to reach a predetermined number as previously described. Namely, in the case of moving a photodetection region at a scanning speed u over a time $\tau$ in a sample solution having a certain particle concentration C, if the cross-sectional area of the photodetection region is taken to be S, then the number of detected particle signals X is represented by equation (10) indicated below.

$$X = CSu\tau N_A \qquad (10)$$

Here, $N_A$ is Avogadro's number. Thus, when a time T is assumed to be required for the number of signals to reach a predetermined number X, then particle concentration C is given as a function of time T according to equation (11).

$$C = XE/(STuN_A) \qquad (11)$$

Furthermore, in Equation (11), particle detection velocity V per unit time is given by equation (12) based on the time T required for the number of signals to reach a predetermined number XE and the number of detected particles XE.

$$V = XE/T \qquad (12)$$

Accordingly, particle concentration C is represented by equation (13).

$$C = V/(SuN_A) \qquad (13)$$

In this equation (13), since particle concentration C is proportional to detection velocity V on the first order, and the correspondence between particle concentration C and detection velocity V is easily understood, particle concentration C may be determined using detection velocity V during actual experimentation.

(ii) Processing Operating Procedure

Figure 5:
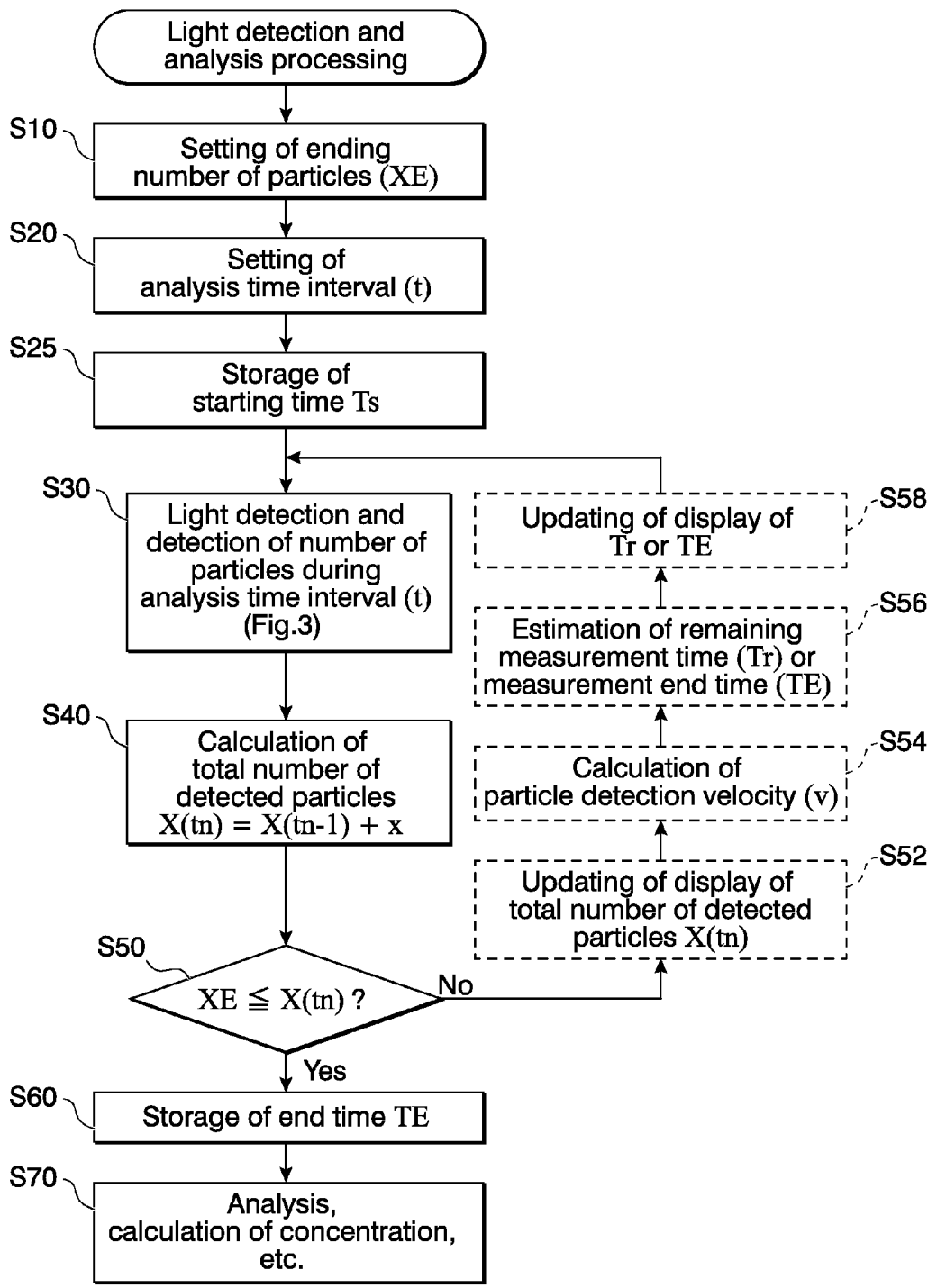
FIG. 5 is a drawing representing another aspect of the processing procedure of an inverse scanning molecule counting method in the form of a flow chart.

Single particle detection processing for detecting a fixed number of signals is carried out according to, for example, the processing procedure indicated in the flow chart of FIG. 5. In the example of FIG. 5, in plain terms, the series of processing consisting of moving the location of the photodetection region, detecting light from the photodetection region, detecting single particle signals and counting the number of detected particle signals; is repeatedly carried out for each analysis time interval t (prescribed time interval) until the number of detected particles X reaches an ending number of particles XE (predetermined number to be reached by the number of luminescent particles). Furthermore, the series of processing and configurations described below should be understood as being realized by processing operations of the computer 18.

(a) Initial Settings

The following provides a detailed explanation of operational processing with reference to FIG. 5. First, a sample solution is injected into the wells 10 of the microplate 9 and the microplate 9 is placed on the stage of the microscope. Subsequently, when a user inputs instructions to the computer 18 to start processing for measuring light intensity and detecting and counting the number of particles, the computer 18 makes initial settings consisting of setting the ending number of particles XE (S10) and setting the analysis time interval t (S20). The ending number of particles XE and the analysis time interval t may also be arbitrarily set by a user. The ending number of particles XE can be suitably determined by referring to results obtained from a preliminary experiment using a solution having a known particle concentration so as to enable a required level of accuracy to be attained for the result of particle concentration. An arbitrary time interval sufficiently shorter than the amount of time from the start of processing until the number of particles (X) reaches the ending number of particles (XE) is suitably set for the analysis time interval t in consideration of, for example, processing speed of the device 1. In addition, the ending number of particles XE and the analysis time interval t may be such that values predetermined by referring to results obtained from a preliminary experiment using a solution having a known particle concentration may be stored in the device 1, and the stored values may be used by being selected automatically or by a user.

(b) Detection of Number of Particles

Once the ending number of particles XE and the analysis time interval t have been set in the manner described above, processing for measurement of light intensity using the scanning molecule counting method over the analysis time interval t as well as detection of particle signals from the measured light intensity data and detection of the number of particles x (S30) and processing for determining the total number of particles $X(t_n)$ by accumulating the detected number of particles x in S30 (S40) are repeatedly carried out for each analysis time interval t until the total number of particles $X(t_n)$ reaches the ending number of particles XE (S50). Furthermore, prior to repeatedly carrying out the processing of S30 to S50, a starting time Ts for this series of processing is stored in memory (S25).

The processing for detecting light intensity and detecting the number of particles of S30 is the same as the processing indicated in FIG. 3. In plain terms, measurement of light intensity is carried out over the analysis time interval t while moving the location of the photodetection region in a sample solution (scanning the interior of the sample solution). Subsequently, the computer 18 carries out detection of signals representing the presence of single particles and counting of the number of detected particles in the resulting chronological light intensity data during the analysis time interval t by processing in accordance with a program stored in a memory device thereof.

Thus, when the number of particles x is detected in chronological light intensity data over the analysis time interval t, the total number of detected luminescent particles X(tn) is calculated using equation (14) (FIG. 5, S40).

$$X(t_n)=X(t_{n-1})+x \quad (14)$$

Furthermore, $X(t_{n-1})$ is the total number of detected particles detected by the time of the previous analysis time interval t, and the initial value thereof is 0. S30 to S40 are then repeated for each analysis time interval t until the total number of detected luminescent particles $X(t_n)$ reaches the ending number of particles XE, namely until equation (15) is satisfied (S50).

$$X(t_n) \geq XE \quad (15)$$

When equation (15) is satisfied during the course of repeating S30 to S50, processing for measuring light intensity of the sample solution and detecting and counting particles is completed. When the repetitive processing of S30 to S50 is completed, an end time TE may be stored in memory (S60).

(c) Display of Number of Particles and Measurement End Time

During the period when S30 to S50 are repeatedly carried out for each analysis time interval t (until equation (15) is satisfied), the total number of detected particles $X(t_n)$ and/or the measurement end time TE or remaining measurement time Tr may be displayed on a display such as a monitor of the computer 18. This configuration is advantageous in that a user is able to predict when measurement will be completed while measurement is in progress by viewing these parameters on the display.

In the case of displaying parameters in the manner described above, each process encircled with dotted lines in the drawing is carried out in the case equation (15) is not satisfied in the judgment of S50 of FIG. 5. More specifically, the most recent total number of detected particles $X(t_n)$ calculated in S40 is first displayed on the display (S52). Furthermore, in the case S30 to S50 have already been repeated, the previous value of the total number of detected particles $X(t_n)$ is updated. Next, in order to determine the measurement end time TE or remaining measurement time Tr, the particle detection velocity v is calculated from the start of the processing of S30 to S50 (S54). The current particle detection velocity v is given by equation (16).

$$v=X(t_n)/(T_p-T_s) \quad (16)$$

Here, $T_p$ is the current time. Thus, remaining measurement time Tr (time until completion of the processing of S30 to S50) is estimated using particle detection velocity v according to equation (17).

$$Tr=(XE-X(t_n))/v \quad (17)$$

In addition, measurement end time TE (time at which the processing of S30 to S50 is completed) is estimated according to equation (18) (S56).

$$TE=T_p+Tr \quad (18)$$

The estimated measurement end time TE or remaining measurement time Tr is then displayed on the display (S58). Furthermore, previously displayed values are updated in the case S30 to S50 have already been repeated. In addition, when $X(t_n)=0$, calculations using equations (17) and (18) are not carried out and Tr and TE are not displayed since they are unknown.

The processing of the aforementioned S30 to S50 of FIG. 5 is repeated for each analysis time interval t as previously described. With respect to this point, the measurement of light intensity of S100 in FIG. 3 is continuously carried out, even while signal processing procedure other than S100 are being carried out, from the start to completion of measurement. Namely, during processing for detecting light and detecting the number of particles, when one cycle of measurement of light intensity over the analysis time interval t is completed, simultaneous to the next cycle of measurement of light intensity over the analysis time interval t being continued to be carried out, the computer 18 carries out processing for detecting and counting particle signals from light intensity data of the completed cycle acquired over the analysis time interval t. As a result, real-time particle detection and counting are achieved.

(d) Analyses for Calculation of Concentration and Other Parameters

When the number of particles has reached the ending number of particles, analyses for calculating concentration and other parameters are carried out using the amount of time T until the number of particles reaches the ending number of particles ($=TE-T_s$) or other information obtained from detected particle signals (S70). As was previously described, particle concentration is determined from particle detection velocity V using the relationship of equation (13) by determining the particle detection velocity V from the time T until the ending number of particles is reached and the ending number of particles XE using equation (12).

Furthermore, although the cross-sectional area S of the region through which the photodetection region has passed in equations (10) to (13) may be determined theoretically based on the wavelength of excitation light or detection light, the numerical aperture of the lens and the adjusted state of the optical system, it may also be determined experimentally from the number of detected particles and concentration of luminescent particles in a control solution by measuring light intensity and detecting and counting particles as previously explained for a solution having a known particle concentration (control solution) under the same conditions as measurement of the sample solution to be tested. More specifically, if the number of detected particles during measurement of light intensity carried out over a certain time τo at a movement speed uo for a control solution having a particle concentration C, for example, is taken to be N, then the cross-sectional area S of the of the region through which the photodetection region has passed is given by equation (19).

$$S = N/(C \cdot NA \cdot uo \cdot to) \qquad (19)$$

In addition, a plurality of solutions having different particle concentrations may be provided for use as control solutions, measurements may be carried out on each control solution, and the average value of the calculated S may be used as the cross-sectional area S of the region through which the photodetection region has passed.

Figure 6A:
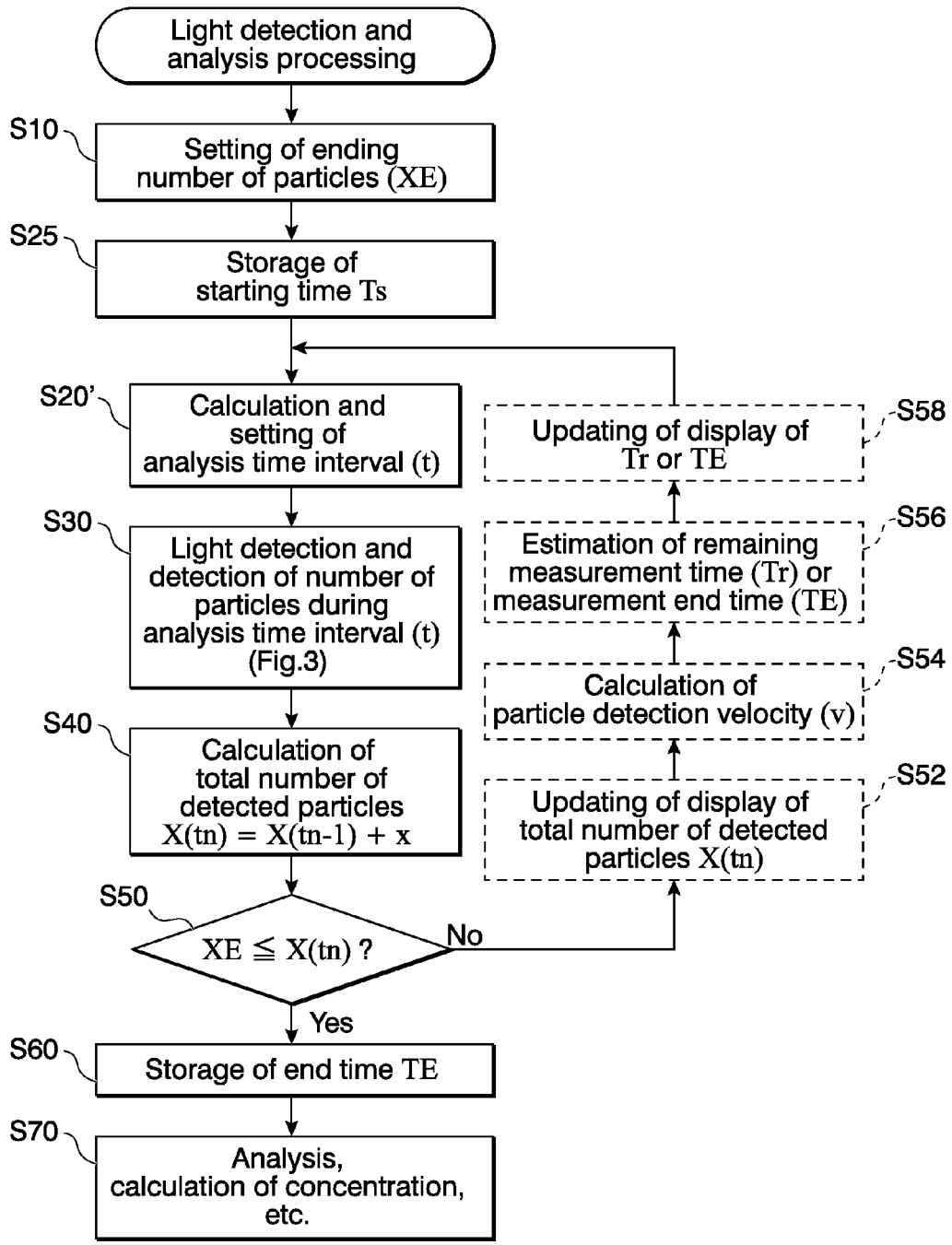
FIG. 6A is a drawing representing still another aspect of the processing procedure of an inverse scanning molecule counting method in the form of a flow chart.
Figure 6B:
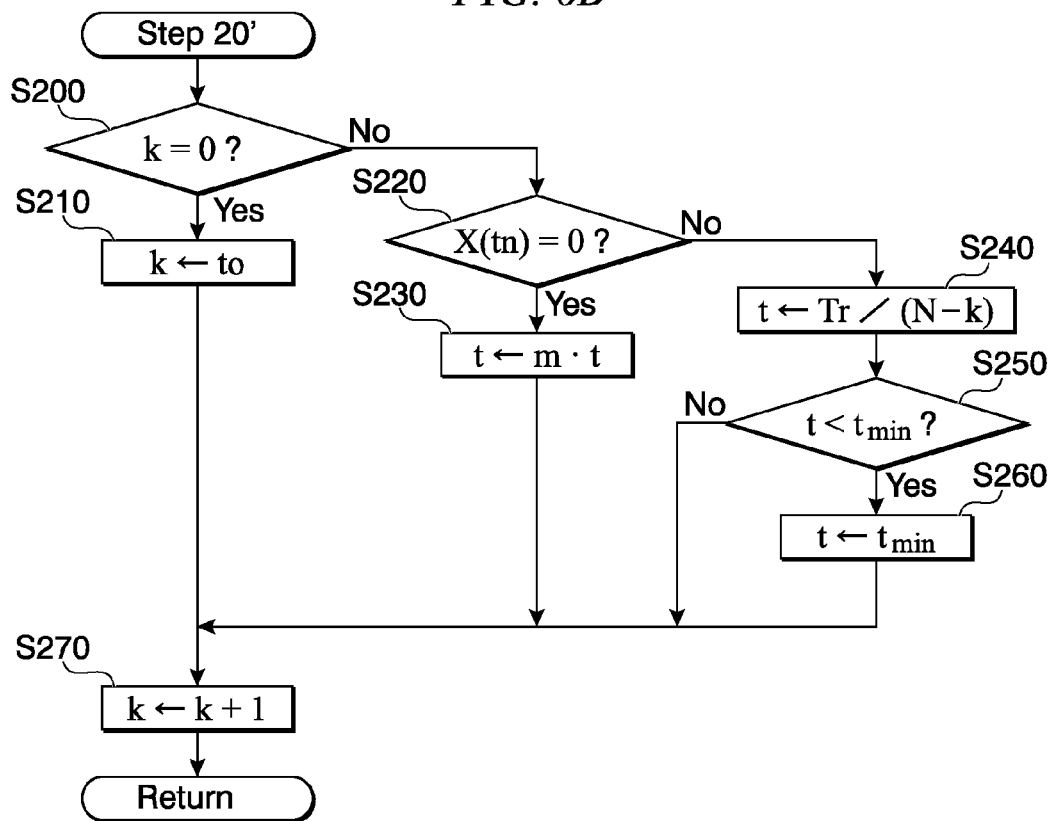
FIG. 6B is a drawing representing still another aspect of the processing procedure of an inverse scanning molecule counting method in the form of a flow chart.

(e) Example of Revision of Processing for Measuring Light Intensity and Detecting and Counting Particles of Sample Solution As another aspect of the aforementioned processing for measuring the light intensity and detecting and counting luminescent particles in a sample solution, the analysis time interval t may not be fixed, but rather may be revised corresponding to the detection status of the luminescent particles. FIG. 6A represents processing for measuring light intensity and detecting and counting particles in a sample solution composed so as to include processing for revising the analysis time interval t corresponding to particle detection status (S20') in the form of a flow chart. FIG. 6B represents arithmetic processing of the analysis time interval in S20' in the form of a flow chart. Furthermore, in FIG. 6A, the same numbering is used to indicate processing that is the same as that of FIG. 5.

In the processing of FIG. 6A, the analysis time interval t is revised each time measurement of light intensity over the analysis time interval t is completed (S20'). In addition, the example of processing shown in the drawings is particularly composed so that a processing cycle consisting of measuring light intensity and detecting and counting particles is carried out for a predetermined number of times N (to be referred to as the "scheduled number of updates") in a single measurement from the start of processing until the number of particles reaches the ending number of particles XE. More specifically, after first setting the ending number of particles XE (S10) and storing the starting time Is in memory (S25) as initial settings, when first carrying out processing for measuring light intensity and detecting and counting particles, namely when the number of processing cycles carried out for measuring light intensity and detecting and counting particles is 0, an arbitrarily set initial value to is assigned to the analysis time interval t (refer to S200 and S210 of FIG. 6B). The number of processing cycles carried out, k, is then increased by 1 (S270), and processing for measuring light intensity and detecting and counting particles over the analysis time interval t is carried out in the same manner as the processing described in FIG. 5 (S30 to S50). Thus, when the number of particles x (=$X(t_1)$) of the first cycle is obtained, particle detection velocity v (S54) and remaining measurement time Tr (S56) are determined in that order. Furthermore, similar to the case of FIG. 5, the total number of detected particles $X(t_n)$ and/or the measurement end time TE or remaining measurement time Tr may be displayed on a display such as a monitor of the computer 18 (S52 and S58). In addition, when the number of particles has reached the ending number of particles XE in the first cycle, processing for measuring light intensity and detecting and counting particles is completed (S50).

Following the initial processing cycle, a processing cycle for revising the analysis time interval t and measuring light intensity and detecting and counting particles in the same manner as in the case of FIG. 5 (S20' and S30 to S58) is repeated until the number of particles reaches the ending number of particles XE. At this time, in S20' for revising the analysis time interval t, a judgment is first made as to whether or not the number of particles $X(t_n)$ detected until that time is 0 (S220). If $X(t_n)$=0, the analysis time interval t of the cycle immediately before is multiplied by m (where, m is an interval of 1 or more). If $X(t_n)$>0, the analysis time interval t is determined according to equation (20) using the remaining measurement time Tr, the scheduled number of updates N and the number of times k the processing cycle is carried out (S240).

$$t = Tr/(N-k) \qquad (20)$$

Furthermore, a lower limit is set for the determined analysis time interval t, and when the analysis time interval t is less than the lower limit value tmin, the analysis time interval t is set to the lower limit value tmin (S250 and S260). As was previously described, according to this aspect in which the analysis time interval t is revised, since the detection status of particles in the sample solution targeted for observation is reflected in the remaining measurement time Tr, the analysis time interval t is optimized corresponding to that particle detection status.

<Target Particle Detection Method>

The detection method of the present embodiment detects a non-luminescent particle dispersed and randomly moving in a solution. As was previously described, the inverse scanning molecule counting method is able to measure particles at an extremely low concentration on the pM order or lower while the particles are in a discrete state. Consequently, according to the detection method of the present embodiment, a target particle bound to labeling particles can be counted with high sensitivity even in the case the concentration of target particles to be analyzed in a sample solution is extremely low.

Moreover, in the detection method of the present embodiment, as a result of two or more labeling particles, for which the size per molecule is sufficiently small relative to the volume of the photodetection region of the optical system (namely, there is hardly any decrease in light intensity detected from the photodetection region when the particles pass through the photodetection region), being bound to the target particle, a complex having a certain degree of size relative to the volume of the photodetection region is formed. When the aforementioned complex passes through the aforementioned photodetection region, the complex is detected based on a decrease in light intensity detected from the photodetection region. In other words, in the inverse scanning molecule counting method used in the detection method of the present embodiment, since labeling particles that form a complex by binding with the target particle can be detected by distinguishing from free labeling particles not bound to the target particle, it is not necessary to remove the free labeling particles from the sample solution prior to measurement according to the inverse scanning molecule counting method.

More specifically, the method of the present embodiment has the (a) and the (b) indicated below.

(a) preparing a sample solution containing target particles, and labeling particles of which the outer diameter thereof is less than 15% of the diameter of a photodetection region of the optical system, binding two or more molecules of the labeling particles per molecule of the target particles in the sample solution, and forming a non-luminescent complex of which the outer diameter is 15% or more of the diameter of the photodetection region; and, (b) calculating the number of molecules of the complex in the sample solution prepared in the (a), comprising:

moving the location of the photodetection region of the optical system in the sample solution, generating chronological light intensity data by detecting light containing substantially constant background light from the photodetection region while moving the location of the photodetection region of the optical system in the sample solution, individually detecting a decrease in light intensity in the chronological light intensity data that occurs when the complex has entered the photodetection region as a signal representing the presence of an individual complex, and counting the number of the complexes detected during movement of the location of the photodetection region by counting the number of signals representing the presence of the individually detected complex.

The target particles targeted for detection in the detection method of the present embodiment may be any arbitrary particles provided they are particles that are dispersed and demonstrate Brownian movement in a sample solution, and there are no particular limitations thereon. Examples of target particles include biomolecules such as proteins, peptides, nucleic acids, nucleic acid-like substances, lipids, saccharides, amino acids or aggregates thereof, particulate biological targets such as viruses or bacteria, and non-biological particles (such as atoms, molecules, micelles or metal colloids). Nucleic acids may be DNA or RNA, or may be artificially amplified in the manner of cDNA. Examples of nucleic acid-like substances include substances in which side chains and the like of naturally-occurring nucleotides (nucleotides present in nature) in the manner of DNA or RNA have been modified by functional groups such as an amino group, and substances that have been labeled with a protein or low molecular weight compound and the like. Specific examples of nucleic acid-like substances include bridged nucleic acids (BNA), nucleotides in which an oxygen atom at position 4' of a naturally-occurring nucleotide has been substituted with a sulfur atom, nucleotides in which a hydroxyl group at position 2' of a naturally-occurring nucleotide has been substituted with a methoxy group, hexitol nucleic acids (HNA) and peptide nucleic acids (PNA).

The target particle in the detection method of the present embodiment may be a nucleic acid molecule or nucleic acid-like substance. The nucleic acid molecule or nucleic acid-like substance may be a double-stranded nucleic acid molecule or single-stranded nucleic acid molecule. Specific examples thereof include a nucleic acid molecule having a base sequence present in the chromosome of an animal or plant or in the gene of a bacterium or virus, and a nucleic acid molecule having an artificially designed base sequence. Among these, the target particle may be micro RNA, siRNA, mRNA, hnRNA, genomic DNA, synthetic DNA obtained by PCR or other amplification, or cDNA synthesized from RNA using a reverse transcriptase.

The labeling particles used in the detection method of the present embodiment are such that the size per molecule is sufficiently small to a degree that there is hardly any decrease in light intensity detected from a photodetection region when the particles pass through the aforementioned photodetection region, and as a result of two or more labeling particles being bound to a single molecule of target molecules, a complex having a certain degree of size is formed to a degree that the degree of the decrease in light intensity detected from the aforementioned photodetection region increases significantly in comparison with that of being in the state of a single molecule. Consequently, according to the inverse scanning molecule counting method, free labeling particles not bound to target particles and labeling particles that have formed a complex by binding with the target particles can be distinguished and counted.

The size of the labeling particle is that to a degree at which there is hardly any decrease in light intensity detected from a photodetection region when the particle passes through the aforementioned photodetection region, and can be suitably determined in consideration of the photodetection region of the optical analysis device used for measurement according to the inverse scanning molecule counting method and the wavelength and light intensity of detected background light. In the present embodiment, since there are hardly any decreases in the light intensity of background light observed when in the state of a single molecule, the average outer diameter of the labeling particle may be less than 15%, or less than 10%, of the diameter of the photodetection region of the aforementioned optical system.

The size of the complex in which two or more labeling particles are bound to a target particle is such that the degree of the decrease in light intensity detected from a photodetection region increases significantly in comparison with the case of a single molecule of the labeling particles when the aforementioned particles pass through the aforementioned photodetection region, and can be suitably determined in consideration of the photodetection region of the optical analysis device used for measurement according to the inverse scanning molecule counting method and the wavelength and light intensity of detected background light. In the present embodiment, the outer diameter of the complex may be 15% or more, or 35% or more, of the diameter of the photodetection region of the aforementioned optical system.

The number of labeling particles that bind per molecule of target particles is two or more, and can be suitably determined in consideration of the size per molecule of the target particle and labeling particle, and the size of the complex. In the present embodiment, the number of labeling particles that bind per molecule of target particles may be as large as possible in order to be able to make the difference with the size of the complex obtained by binding with the target particle sufficiently large.

In the detection method of the present embodiment, the complex is a non-luminescent particle. For example, both the target particle and labeling particle may be non-luminescent particles, or the target particle may be a fluorescent particle and the labeling particle may be a quencher that absorbs fluorescent light emitted from the aforementioned fluorescent substance.

The labeling particle consists of a substance having a site that specifically or non-specifically binds or adsorbs to the target particle. For example, in the case the target particle is a nucleic acid molecule or a nucleic acid-like substance, examples of the labeling particle includes an oligonucleotide that hybridizes with the target particles, a nucleic acid-binding protein (such as a nucleic acid-binding antibody) and a non-luminescent dye molecule that binds to nucleic acids. The oligonucleotide may be DNA or RNA, may be artificially amplified in the manner of cDNA, or may contain all or a portion of a nucleic acid-like substance capable of forming nucleotide chains and base pairs in the same manner as naturally-occurring nucleic acid bases.

In addition, in the case the target particle is a protein, an antigen or antibody to the target particle or a ligand or receptor for the target particle can be used for the labeling particle.

Although the labeling particles used in the present embodiment may be those which bind non-specifically to the target particles, from the viewpoint of accuracy of detection and quantitative determination of target particles, labeling particles can be those that bind specifically. Furthermore, labeling particles that specifically bind to the target particles are only required to be a substance that preferentially binds to the target particle rather than binding to other substances having physical or chemical properties similar to those of the target particle, and are not required to be a substance that does not bind at all to substances other than the target particles. For example, in the case the target particle is a nucleic acid molecule, an oligonucleotide used as a labeling particle may have a base sequence that is completely complementary to a partial base sequence of the aforementioned target particle, or may have abase sequence that contains one or several base mismatches with a partial base sequence of the aforementioned target particle.

Particles provided with a substance that specifically or non-specifically binds with target particles (to be referred to as a "substance that binds with a target particle") on the surface thereof can also be used for the labeling particle. Examples of the aforementioned particles include magnetic particles, silica particles, agarose gel particles, polyacrylamide resin particles, latex particles, polystyrene and other plastic particles, ceramic particles and zirconia particles.

In the case of using a particle provided with a substance that binds with the target particle on the surface thereof for the labeling particle, a plurality of substances that bind with the target particle is normally bound to the particle surface. Consequently, the use of such a particle enables the target particle and labeling particle to aggregate and form a larger complex. Furthermore, a substance that binds with one type of target particle may be bound to the surface of a single particle or a substance that binds with two or more types of target particles may be bound thereto.

There are no particular limitations on the method used to bind a substance that specifically or non-specifically binds or adsorbs to target particle to the surface of the particle, and may be physically adsorbed or chemically bound to a functional group on the particle surface. In the case of being chemically bound, the substance can be bound using a method that is suitable for each functional group. For example, examples of such methods include the use of an EDAC reaction, a reaction in which carbonic acid and an amino group are bound by preliminarily mixing EDC and NHS, and a reaction in which an activated aldehyde group or tosyl group bonds to a functional group in a substance that specifically or non-specifically binds or adsorbs to a target particle. In the case of a magnetic particle not having a functional group on the particle surface, the particle surface may be coated with functional groups.

In the present embodiment, a plurality of labeling molecules is allowed to simultaneously bind to a single molecule of a target particle, and one type of labeling particle may be used or two or more types of labeling particles may be used. For example, in the case of sites having the same structure being present at a plurality of locations on a target particle, one type of substance that specifically or non-specifically binds or adsorbs to the aforementioned sites may be used for the labeling particle. In addition, a plurality of substances capable of independently binding with respectively different sites on a target particle may also be used as labeling particles. For example, in the case the target particle is a nucleic acid molecule or nucleic acid-like substance, a plurality of oligonucleotides that hybridize with respectively different partial regions of the target particle can be used as labeling particles.

More specifically, in the (a), target particles and labeling particles are added to a suitable solvent to prepare a solution that contains both. There are no particular limitations on the aforementioned solvent provided it does not damage the target particles or labeling particles. Although the solvent is typically an aqueous solution, it may also be an organic solvent such as formamide or other arbitrary liquid. More specifically, the aforementioned solvent can be suitably selected and used from among buffers commonly used in the art. Examples of the aforementioned buffers include phosphate buffers or Tris buffers, such as phosphate-buffered saline (PBS, pH 7.4).

Although there are no particular limitations on the concentration of the labeling particles added to the solution, a solution containing both labeling particles and target particles may be prepared so that the concentration of the labeling particles is higher than the concentration obtained by multiplying the number of labeling particles able to bind per molecule of target particles by the expected concentration of target particles in order to enhance detection sensitivity of the target particles.

Next, a complex is formed by allowing two or more of the aforementioned labeling particles to bind per molecule of the aforementioned target particles in the sample solution. In the case of being able to bind the target particles and the labeling particles by simply having them both present in the same solution, a complex containing the target particles and the labeling particles can be formed in the aforementioned solution simply by preparing a solution containing both followed by incubating the solution for a prescribed amount of time as necessary.

On the other hand, in the case the target particle and the labeling particle are nucleic acid molecules or nucleic acid-like substances having a double-stranded structure, the target particles and labeling particles may be associated after having denatured the nucleic acid molecules and the like in the solution. Furthermore, "denaturing nucleic acid molecules or nucleic acid-like substances" refers to the dissociation of base pairs. For example, this refers to denaturing a double-stranded nucleic acid molecule to a single-stranded nucleic acid molecule. Furthermore, in the case the labeling particle is an oligonucleotide containing a nucleic acid like-substance such as PNA, even if the target particle is a double-stranded nucleic acid molecule, a complex containing the aforementioned labeling particles and target particle may be able to be formed without having to carry out special denaturation treatment.

Examples of denaturation treatment include denaturation by high-temperature treatment (heat denaturation) and denaturation by low salt concentration treatment. In particular, it can be heat denaturation since the procedure is simple. More specifically, in the case of heat denaturation, nucleic acid molecules and the like in a solution can be denatured by subjecting the aforementioned solution to high-temperature treatment. In general, although nucleic acid molecules can be denatured by warming at a temperature of 90° C. for DNA or 70° C. for RNA for several seconds to about 2 minutes, since the denaturing temperature varies according to the base length of the target particle, the aforementioned warming temperature and warming time are not limited thereto provided denaturation is possible. On the other hand, denaturation by low salt concentration treatment can be carried out by, for example, adjusting the salt concentration of the aforementioned solution to be sufficiently low by diluting with purified water and the like.

After having denatured as necessary, the target particles and the labeling particles in the aforementioned solution are associated to form a complex containing both. In the case of having carried out heat denaturation, both the target particles and labeling particles in the solution can be suitably associated by lowering the temperature of the aforementioned solution to a temperature that allows the target particles and labeling particles to specifically hybridize (specific association conditions) following heat denaturation. The temperature of the solution containing both the target particles and labeling particles may be lowered to a temperature of about ±3° C. of the Tm value of the region in the labeling particles having a complementary base sequence to the target particles. In addition, in the case of having carried out denaturation by low salt concentration treatment, the target particles and labeling particles in the aforementioned solution can be suitably associated by raising the salt concentration of the solution to a concentration that allows specific hybridization between the target particles and labeling particles by adding a salt solution and the like.

Furthermore, the temperature at which two single-stranded nucleic acid molecules are able to specifically hybridize can be determined from a melting curve of an association product composed of the target particles and labeling particles. A melting curve can be determined by, for example, changing the temperature of a solution containing only the target particles and labeling particles from a high temperature to a low temperature and measuring optical absorbance or fluorescence intensity of the solution. The temperature range from the temperature at which the two denatured single-stranded nucleic acid molecules begin to form an association product to the temperature at which the nucleic acid molecules have nearly completely formed an association product as determined from the resulting melting curve can be taken to be the temperature range over which both are able to specifically hybridize. The concentration at which two single-stranded nucleic acid molecules can specifically hybridize can be determined by similarly determining a melting curve by changing the salt concentration in a solution from a low concentration to a high concentration instead of changing the temperature.

In this manner, although specific association conditions vary for each type of target particle and labeling particle and are determined experimentally, the conditions can ordinarily be substituted with melting temperature (Tm). For example, the Tm value of a region that hybridizes with a target particle (temperature at which 50% of double-stranded DNA dissociates to single-stranded DNA) can be calculated from base sequence information of the labeling particle by using commonly used primer/probe design software and the like. Conditions under which the temperature is in the vicinity of the Tm value, and for example, conditions under which the temperature is within about ±3° C. of the Tm value, can be used as specific association conditions. More detailed specific association conditions can be determined by experimentally determining a melting curve at a temperature in the vicinity of the calculated Tm value.

In addition, in order to suppress non-specific hybridization, the temperature of the aforementioned solution may be lowered comparatively slowly when forming a complex. For example, after having denatured a nucleic acid molecule by making the temperature of the aforementioned solution to be 70° C. or higher, the liquid temperature of the solution can be lowered at a temperature lowering rate of 0.05° C./second or faster.

In addition, in order to suppress non-specific hybridization, a surfactant, formamide, dimethylsulfoxide or urea and the like may be added to the aforementioned solution in advance. Only one type of these compounds may be added or two or more types may be added in combination. The addition of these compounds makes it possible to make it difficult for non-specific hybridization to occur in a comparatively low-temperature environment.

Subsequently, in the (b), the number of molecules of the aforementioned complex in the sample solution prepared in the (a) is calculated according to the inverse scanning molecule counting method. More specifically, a sample solution is placed in an optical analysis device for measuring according to the aforementioned inverse scanning molecule counting method. As a result of the aforementioned procedure, chronological light intensity data is generated by detecting light containing substantially constant background light from a photodetection region while moving the location of the aforementioned photodetection region of the optical system within the sample solution. Decreases in light intensity that occur when the complex has entered the photodetection region are individually counted as signals representing the presence of each complex in the resulting chronological light intensity data. The number of the aforementioned complexes detected during movement of the location of the photodetection region is then counted by counting the number of signals representing the presence of the individually detected complexes.

In the case of counting according to the inverse scanning molecule counting method, the substantially constant background light to be contained in light from the photodetection region may be illumination light such as that obtained by transillumination, or may be fluorescent light, phosphorescent light, chemiluminescent light, bioluminescent light or scattered light generated by a substance dispersed in a sample solution. In this case, in the case a substance that releases or scatters light is not dispersed in the solution used for the sample solution, a substance that actively releases or scatters light may be dissolved or dispersed in that solution. In addition, in the case the solution used for the sample solution emits autofluorescent light, that autofluorescent light is used for the aforementioned background light.

In the case of dissolving or dispersing a substance that releases or scatters light in a sample solution in order to generate background light, the aforementioned substance may be added to the sample solution prior to measurement according to the inverse scanning molecule counting method, may be added together with the labeling particles prior to the formation of a complex in the (a), or may be added after the (a). Although the substance is typically a fluorescent substance, it may also be a substance that emits light by phosphorescence, chemiluminescence, bioluminescence or light scattering. There are no particular limitations on the fluorescent substance provided it is a substance that releases fluorescent light as a result of being irradiated with light of a specific wavelength, and can be suitably selected and used from among fluorescent dyes used in FCS or FIDA and the like.

Moreover, the number density or concentration of the aforementioned target particles in the aforementioned sample solution can be determined based on the number of the aforementioned complexes detected and counted in the (b). Information relating to the number density or concentration of complexes identified in the sample solution is obtained by combining the number of detected complexes and the amount of movement of the location of the photodetection region. More specifically, the ratio of the number densities or concentrations of a plurality of sample solutions, or the ratio of the relative number density or concentration relative to a standard sample solution serving as a reference for concentration or number density, for example, is calculated, or the absolute value of number density or concentration is determined using the ratio of number density or concentration relative to a standard sample solution serving as a reference for concentration or number density. Alternatively, the number density or concentration of a complex can be calculated in detail by specifying the total volume of the movement locus of the location of the photodetection region by moving the location of the photodetection region at a prescribed speed, for example, according to an arbitrary technique.

EXAMPLES

Although the following provides a more detailed explanation of aspects of the present invention by indicating examples thereof, the aspects of the present invention are not limited to the following examples.

Reference Example 1

Non-luminescent particles having different diameters were measured according to the inverse scanning molecule counting method using the optical system of a confocal microscope having a diameter of the photodetection region of about 2.8 μm.

First, polystyrene particles (Spherotech, Inc.) having an average particle diameter (average outer diameter) of 0.32 μm, 0.41 μm or 0.92 μm were prepared at a concentration of 20 fM each using a 20% by volume PEG solution to prepare polystyrene particle solutions. Separate from the above, a fluorescent substance in the form of ATTO® 488 (ATTO-TEC Gmbh) was prepared at a concentration of 6 nM using 10 mM Tris buffer (pH 8) to prepare a fluorescent substance solution. Subsequently, equal amounts of the aforementioned polystyrene particle solutions and the aforementioned fluorescent substance solution were mixed to prepare measurement sample solutions. These measurement sample solutions were then measured according to the inverse scanning molecule counting method.

More specifically, the MF20 Single Molecule Fluorescence Spectroscopy System (Olympus Corp.) equipped with the optical system of a confocal fluorescent microscope and a photon counting system was used as an optical analysis device during measurement, and chronological photon count data was acquired for each of the aforementioned sample solutions. Laser light having a wavelength of 488 nm and irradiated at 50 μW was used as excitation light, and chronological light intensity data was generated by measuring light within the wavelength range of 510 nm to 560 nm using a band pass filter. The photodetection region in the sample solution was rotated at a movement speed of 6000 rpm, BIN TIME was set to 10 μs, and measurement time was set to 30 seconds. In addition, measurements were carried out three times each on each sample solution. Chronological data obtained from the measurements was smoothed using the Savitzky-Golay algorithm, followed by detecting peaks by differentiation. Those regions considered to be peaks that were able to approximate a Gaussian function were extracted as signals.

Figure 7:
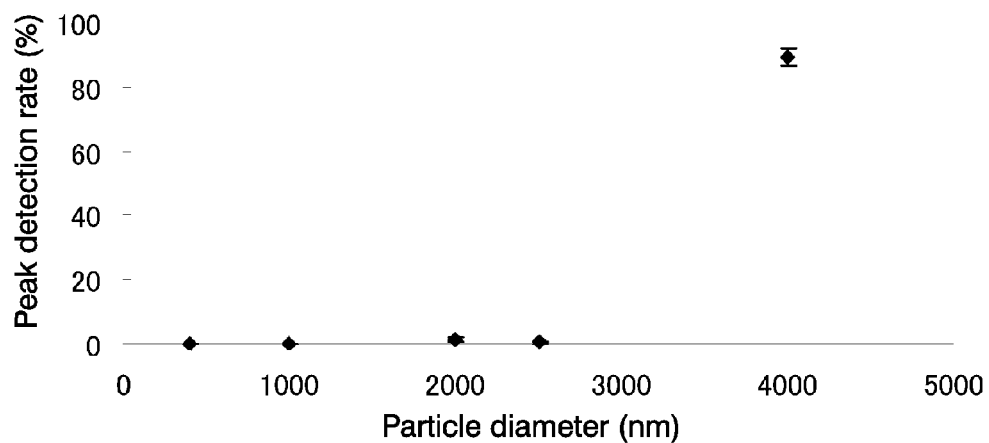
FIG. 7 is a drawing showing the results of calculating peak detection rates in various sample solutions in Reference Example 1.

Peak detection rate (%) was calculated by dividing the actual number of peaks obtained as a result of measuring by the number of peaks calculated from the scanned volume. The calculation results are shown in FIG. 7. In the case of the polystyrene particles having an average particle diameter of 0.32 μm or 0.41 μm, in contrast to peaks not being detected and the peak detection rates both being less than 10% at 5.6% and 4.7%, respectively, in the case of the polystyrene particles having an average particle diameter of 0.92 μm, the peak detection rate was 85.7%. On the basis of these results, particles having an outer diameter smaller than the diameter of the photodetection region were confirmed to not be detected in the inverse scanning molecule counting method.

Example 1

Target particles in a sample solution were detected according to the inverse scanning molecule counting method using the optical system of a confocal microscope having a diameter of the photodetection region of about 2.8 μm, using dextran having a large number of biotinylation sites per molecule (dextran biotin) for the target particles, and using streptavidin particles as labeling particles.

First, streptavidin particles that have streptavidin coated on the surface thereof (average particle diameter: 0.32 μm, Spherotech, Inc.) were prepared at concentrations of 4 pM each using 20% by volume PEG solution (streptavidin particle solutions). In addition, dextran biotin (Invitrogen Corp.) was prepared at concentrations of 0 pM, 20 pM, 200 pM and 2 nM using 10 mM Tris buffer (pH 8) (dextran biotin solutions). Moreover, separate from the above, a fluorescent substance in the form of ATTO® 488 (ATTO-TEC Gmbh) was prepared at a concentration of 6 nM using 10 mM Tris buffer (pH 8) (fluorescent substance solution).

Equal amounts of the streptavidin particle solutions and dextran biotin solutions were mixed, and the resulting mixtures were allowed to stand undisturbed for 30 minutes at room temperature. Subsequently, an equal amount of the fluorescent substance solution was added to the aforementioned mixtures to prepare measurement sample solutions.

Figure 8:
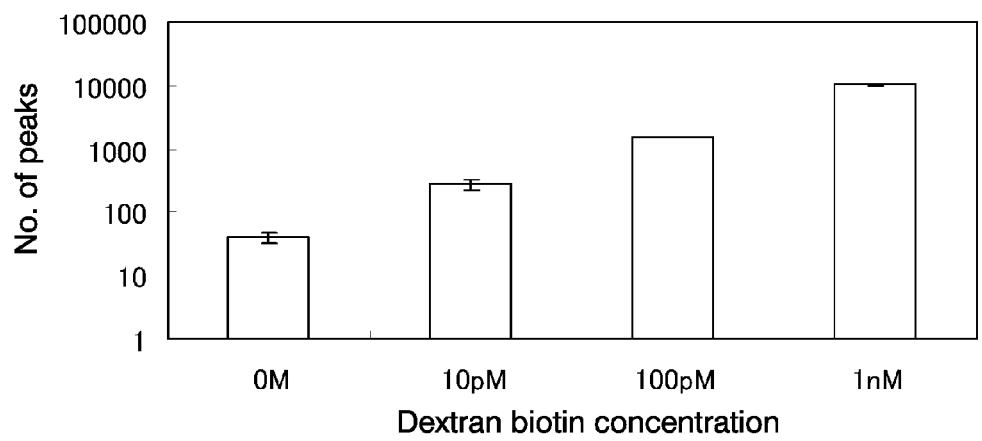
FIG. 8 is a drawing showing the number of peaks obtained from various sample solutions and dextran biotin concentrations in Example 1.

These sample solutions were measured according to the inverse scanning molecule counting method in the same manner as Reference Example 1 with the exception of changing the measurement time to 60 seconds. FIG. 8 is a drawing showing the resulting number of peaks and dextran biotin concentration. As a result, the number of detected peaks increased dependent on the concentration of dextran avidin. In other words, peaks were detected due to the formation of aggregates of dextran biotin and streptavidin particles.

Example 2

Target particles in a sample solution were detected according to the inverse scanning molecule counting method using the optical system of a confocal microscope having a diameter of the photodetection region of about 2.8 μm, using a nucleic acid having zero, one, or two biotinylation sites per molecule for the target particles, and using streptavidin particles as labeling particles.

First, aqueous solutions containing each of the nucleic acids indicated below were prepared (Nucleic Acid Samples 1 to 4). Furthermore, each base sequence is shown in Table 1.

Nucleic Acid Sample 1 consisted of 10 ng/μL of Genome Sample No. 194 provided by the Human Science Research Resources Bank (HSRRB) (to be referred to as "Genome No. 194").

Nucleic Acid Sample 2 consisted of 10 ng/μL, of Genome No. 194 and a PCR product in which one of the nucleic acid strands is composed of the base sequence represented by SEQ ID NO: 1 (to be referred to as the "PCR Product").

Nucleic Acid Sample 3 consisted of 10 ng/μL of Genome No. 194 and a single-stranded nucleic acid composed of the base sequence represented by SEQ ID NO: 2 in which the 5'-terminal was labeled with biotin (to be referred to as "Biotin-ssDNA").

Nucleic Acid Sample 4 consisted of 10 ng/μL, of Genome No. 194 and a double-stranded nucleic acid obtained by association of a single-stranded nucleic acid composed of the base sequence represented by SEQ ID NO: 3 in which the 5'-terminal was labeled with biotin, and a single-stranded nucleic acid composed of the base sequence represented by SEQ ID NO: 4 in which the 5'-terminal was labeled with biotin (to be referred to as "biotin-dsDNA").

TABLE 1

| SEQ ID NO. 1 | TGGATAACCGTATTACCGCCTTTGAGTGAG<br>CTGATACCGCTCGCCGCAGCCGAACGACCG<br>AGCGCAGCGAGTCAGTGAGCGAGGAAGCGG<br>AAGAGCGCCCAATACGCAAACCGCCTCTCC<br>CCGCGCGTTGGCCGATTCATTAATGCAGCT<br>GGCACGACAGGTTTCCCGACTGGAAAGCGG<br>GCAGTGAGCGCAACGCAATTAATGTGAGTT<br>AGCTCACTCATTAGGCACCCCAGGCTTTAC<br>ACTTTATGCTTCCGGCTCGTATGTTGTGTG<br>GAATTGTGAGCGGATAACAATTTCACACAG<br>GAAACAGCTATGACCATGATTACGCCAAGC<br>TTGCATGCCTGCAGGTCGACTCTAGAGGAT<br>CCCCGGGTACCGAGCTCGAATTCACTGGCC<br>GTCGTTTTAC |
|---|---|
| SEQ ID NO: 2 | CTGCAACTTTATCCGCCTCCATCCAGTCTA |
| SEQ ID NO: 3 | GCCACAGAAGAAATCTCCCAAGTATTTCGA<br>TTCTTCAGACTAAAACGTTAAGGCCTTGC |
| SEQ ID NO: 4 | GCAAGGCCTTAACGTTTTAGTCTGAAGAAT<br>CGAAATACTTGGGAGATTTCTTCTGTGGC |

Moreover, streptavidin particles that have streptavidin coated on the surface thereof (average particle diameter: 0.32 μm, Spherotech, Inc.) were prepared at a concentration of 100 pM each using 20% by volume PEG solution (streptavidin particle solutions). In addition, a fluorescent substance in the form of ATTO® 488 (ATTO-TEC Gmbh) was prepared at a concentration of 6 nM using 10 mM Tris buffer (pH 8) (fluorescent substance solution).

Equal amounts of Nucleic Acid Sample 1 and streptavidin solution were mixed and the resulting mixture was allowed to stand for 30 minutes at room temperature. Subsequently, an equal amount of the fluorescent substance solution was added to the aforementioned mixture to prepare Measurement Sample Solution 1. Measurement Sample Solutions 2 to 4 were prepared in the same manner with the exception of respectively using Nucleic Acid Samples 2 to 4 instead of Nucleic Acid Sample 1. These sample solutions were then measured according to the inverse scanning molecule counting method in the same manner as Reference Example 1 with the exception of using a rotating speed of 6000 rpm and changing the measurement time to 30 seconds.

The numbers of peaks (mean) obtained from each sample solution and their standard deviations (SD) are shown in Table 2. As a result, in Sample Solution 3, which contained only one biotin molecule per molecule of nucleic acid and in which only one molecule of streptavidin particles were bound per molecule, the number of peaks obtained (less than 40) was only roughly equal to those of Samples 1 and 2 that did not contain nucleic acid labeled with biotin. In contrast, in Sample Solution 4, which contained only two molecules of biotin per molecule of nucleic acid and in which two molecules of streptavidin were bound per molecule, 148 peaks were detected. This is presumed to be the result of peaks being detected with high sensitivity by the inverse scanning molecule counting method due to the formation of large complexes attributable to the aggregation of a large number of biotin-dsDNA and streptavidin particles. In addition, since Genome No. 194 was contained in these sample solutions, even in the case of similar substances other than the target particles being present in large numbers in the sample solutions, as a result of using labeling particles that specifically bind with the target particles, the target particles were confirmed to be able to detected with the inverse scanning molecule counting method.

TABLE 2

|   | Nucleic Acid in Sample Solution | No. of Peaks | SD |
|---|---|---|---|
| Sample Solution 1 | Genome No. 194 | 36 | 2 |
| Sample Solution 2 | Genome No. 194, PCR Product | 34 | 5 |
| Sample Solution 3 | Genome No. 194, Biotin-ssDNA | 38 | 4 |
| Sample Solution 4 | Genome No. 194, Biotin-dsDNA | 148 | 7 |

INDUSTRIAL APPLICABILITY

According to the detection method of an aspect of the present invention, since target particles only present at an extremely low concentration in a sample solution can be detected by an inverse scanning molecule counting method, the detection method of an aspect of the present invention can be used in fields such as sample analysis and testing in which the concentrations of clinical specimens and other analysis target substances are extremely low.

BRIEF DESCRIPTION OF THE REFERENCE SYMBOLS

1 Optical analysis device (confocal microscope)
2 Light source
3 Single-mode optic fiber
4 Collimator lens
5 Dichroic mirror
6,7,11 Reflecting mirrors
8 Object lens
9 Microplate
10 Well (sample solution container)
12 Condenser lens
13 Pinhole
14 Barrier filter
14a Dichroic mirror or polarizing beam splitter
15 Multi-mode optic fiber
16 Photodetector
17 Mirror light deflector
17a Stage position adjustment device
18 Computer

The invention claimed is:

1. A method for detecting a target particle dispersed and randomly moving in a sample solution using an optical system of a confocal microscope or multi-photon microscope, comprising:
(a) preparing a sample solution containing target particles, and labeling particles of which an average outer diameter is less than 15% of a diameter of a photodetection region of the optical system, and forming a non-luminescent complex of which an outer diameter is 15% or more of the diameter of the photodetection region by binding two or more molecules of the labeling particles to one molecule of the target particles in the sample solution; and,
(b) calculating number of molecules of the complex in the sample solution prepared in step (a), comprising:
moving a location of the photodetection region of the optical system in the sample solution,
generating chronological light intensity data by detecting light containing substantially constant background light from the photodetection region while moving the location of the photodetection region of the optical system in the sample solution, individually detecting a decrease in light intensity in the chronological light intensity data that occurs when the complex has entered the photodetection region as a signal representing the presence of an individual complex, and counting number of the complexes detected during movement of the location of the photodetection region by counting the number of signals representing the presence of the individually detected complexes.

2. The method for detecting a target particle according to claim 1, wherein the outer diameter of the complex is 35% or more of the diameter of the photodetection region.

3. The method for detecting a target particle according to claim 1, wherein the target particle and the labeling particle bind specifically.

4. The method for detecting a target particle according to claim 1, wherein the target particle is a nucleic acid.

5. The method for detecting a target particle according to claim 1, wherein the background light is fluorescent light, phosphorescent light, chemiluminescent light, bioluminescent light, or scattered light generated by a substance dispersed in the sample solution.

6. The method for detecting a target particle according to claim 1, wherein the background light is illumination light.

7. The method for detecting a target particle according to claim 1, wherein the location of the photodetection region is moved at a speed faster than a diffusion movement speed of the complex in the moving of the location of the photodetection region.

8. The method for detecting a target particle according to claim 1, wherein the location of the photodetection region in the sample solution is moved by altering a light path of the optical system in the moving of the location of the photodetection region.

9. The method for detecting a target particle according to claim 1, wherein a single complex is judged to have entered the photodetection region when a signal has been detected having light intensity lower than a prescribed threshold value as determined from the intensity of the background light in the individually detecting of a signal representing the presence of the complex.

10. The method for detecting a target particle according to claim 1, wherein the chronological light intensity data is smoothed; and a downwardly convex, bell-shaped pulsed signal, having intensity below that of a threshold value determined from the intensity of the background light in the smoothed chronological light intensity data, is detected as a signal representing the presence of the complex in the individually detecting of a signal representing the presence of the complex.

11. The method for detecting a target particle according to claim 1, further comprising:

determining number density or concentration of the target particles in the sample solution based on the number of the complexes detected and counted in step (b).

12. The method for detecting a target particle according to claim 1, wherein the moving of the location of the photodetection region of the optical system in the sample solution, the detecting of light containing substantially constant background light from the photodetection region while moving the location of the photodetection region of the optical system in the sample solution, and the detecting of the signal representing the presence of the individual complex, are repeated until number of signals representing the presence of the complex reaches a predetermined number, and concentration of the target particles in the sample solution is determined based on an amount of time required for the number of signals representing the presence of the complex to reach the predetermined number.

* * * * *

SEQUENCE LISTING

<160> NUMBER OF SEQ ID NOS: 4

<210> SEQ ID NO 1
<211> LENGTH: 400
<212> TYPE: DNA
<213> ORGANISM: Artificial Sequence
<220> FEATURE:
<223> OTHER INFORMATION: Description of Artificial Sequence: PCR
      product.

<400> SEQUENCE: 1
tggataaccg tattaccgcc tttgagtgag ctgataccgc tcgccgcagc cgaacgaccg      60
agcgcagcga gtcagtgagc gaggaagcgg aagagcgccc aatacgcaaa ccgcctctcc     120
ccgcgcgttg gccgattcat taatgcagct ggcacgacag gtttcccgac tggaaagcgg     180
gcagtgagcg caacgcaatt aatgtgagtt agctcactca ttaggcaccc caggctttac     240
actttatgct tccggctcgt atgttgtgtg gaattgtgag cggataacaa tttcacacag     300
gaaacagcta tgaccatgat tacgccaagc ttgcatgcct gcaggtcgac tctagaggat     360
ccccgggtac cgagctcgaa ttcactggcc gtcgttttac                           400

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence:
      Biotin-ssDNA.

<400> SEQUENCE: 2 ctgcaactt atccgcctcc atccagtcta                                       30

<210> SEQ ID NO 3
<211> LENGTH: 59
<212> TYPE: DNA
<213> ORGANISM: Artificial Sequence
<220> FEATURE:
<223> OTHER INFORMATION: Description of Artificial Sequence:
      Oligonucleotide for Biotin-dsDNA.

<400> SEQUENCE: 3
gccacagaag aaatctccca agtatttcga ttcttcagac taaaacgtta aggccttgc      59

<210> SEQ ID NO 4
<211> LENGTH: 59
<212> TYPE: DNA
<213> ORGANISM: Artificial Sequence
<220> FEATURE:
<223> OTHER INFORMATION: Description of Artificial Sequence:
      Oligonucleotide for Biotin-dsDNA.

<400> SEQUENCE: 4
gcaaggcctt aacgttttag tctgaagaat cgaaatactt gggagatttc ttctgtggc      59